(12) United States Patent
Wallace et al.

(10) Patent No.: US 11,986,196 B2
(45) Date of Patent: May 21, 2024

(54) THROMBECTOMY APPARATUSES AND METHODS

(71) Applicant: Boston Scientific Scimed, Inc., Maple Grove, MN (US)

(72) Inventors: Michael P. Wallace, Pleasanton, CA (US); Roy Leguidleguid, Union City, CA (US); Jayson Delos Santos, Fremont, CA (US); Winnie Tang, Santa Clara, CA (US); Michael Turovskiy, San Leandro, CA (US); Robert Garabedian, Mountain View, CA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 80 days.

(21) Appl. No.: 17/519,551

(22) Filed: Nov. 4, 2021

(65) Prior Publication Data

US 2022/0257269 A1 Aug. 18, 2022

Related U.S. Application Data

(60) Provisional application No. 63/249,561, filed on Sep. 28, 2021, provisional application No. 63/151,054, filed on Feb. 18, 2021.

(51) Int. Cl.
*A61B 17/221* (2006.01)
*A61B 17/32* (2006.01)
(Continued)

(52) U.S. Cl.
CPC ...... *A61B 17/221* (2013.01); *A61B 17/32075* (2013.01); *A61B 2017/00292* (2013.01);
(Continued)

(58) Field of Classification Search
CPC ............ A61B 17/221; A61B 17/32075; A61B 2017/00292; A61B 2017/00367;
(Continued)

(56) References Cited

U.S. PATENT DOCUMENTS

| 5,192,268 A | 3/1993 | Shiber |
| 5,431,676 A * | 7/1995 | Dubrul ............... A61B 17/3439 606/191 |

(Continued)

FOREIGN PATENT DOCUMENTS

| EP | 2063791 B1 | 12/2016 |
| EP | 3539486 A1 | 9/2019 |

(Continued)

OTHER PUBLICATIONS

Deaton et al.; U.S. Appl. No. 17/519,533 entitled "Thrombectomy apparatuses," filed Nov. 4, 2021.
(Continued)

*Primary Examiner* — Tan-Uyen T Ho
*Assistant Examiner* — Osama Nemer
(74) *Attorney, Agent, or Firm* — Seager, Tufte & Wickhem, LLP

(57) ABSTRACT

Methods and apparatuses for removing material (e.g., clot) from within a body, including inverting thrombectomy apparatuses. These methods and apparatuses may include methods and apparatuses for reusing portion of the devices, method and apparatuses for loading and reloading the inverting thrombectomy apparatuses, and methods and apparatuses for improving and enhancing the ability of the inverting thrombectomy apparatuses to remove clot.

20 Claims, 22 Drawing Sheets

(51) Int. Cl.
*A61B 17/3207* (2006.01)
*A61M 25/00* (2006.01)
*A61M 25/06* (2006.01)
*A61B 17/00* (2006.01)
*A61M 25/01* (2006.01)

(52) U.S. Cl.
CPC .............. *A61B 2017/00367* (2013.01); *A61B 2017/00867* (2013.01); *A61B 2017/2215* (2013.01); *A61B 2017/320008* (2013.01); *A61B 2017/320741* (2013.01); *A61M 25/0074* (2013.01); *A61M 25/0119* (2013.01); *A61M 25/0668* (2013.01)

(58) Field of Classification Search
CPC .. A61B 2017/00867; A61B 2017/2215; A61B 2017/320008; A61B 2017/320741; A61B 2090/0813; A61B 50/20; A61B 50/33; A61B 2017/22034; A61M 25/0074; A61M 25/002; A61M 25/0119; A61M 25/0668

See application file for complete search history.

(56) References Cited

U.S. PATENT DOCUMENTS

| | | | |
|---|---|---|---|
| 5,441,504 A * | 8/1995 | Pohndorf | A61M 25/0668 604/167.03 |
| 5,762,630 A * | 6/1998 | Bley | A61L 29/14 604/524 |
| 6,135,991 A | 10/2000 | Muni et al. | |
| 6,290,692 B1 * | 9/2001 | Klima | A61M 25/0052 604/524 |
| 6,391,044 B1 | 5/2002 | Yadav et al. | |
| 6,565,583 B1 | 5/2003 | Deaton et al. | |
| 6,605,074 B2 | 8/2003 | Zadno Azizi et al. | |
| 6,632,236 B2 | 10/2003 | Hogendijk | |
| 7,029,488 B2 | 4/2006 | Schönholz et al. | |
| 7,713,227 B2 | 5/2010 | Wholey et al. | |
| 7,909,798 B2 * | 3/2011 | Osypka | B29C 48/12 604/161 |
| 7,989,207 B2 | 8/2011 | Soito et al. | |
| 8,052,640 B2 | 11/2011 | Fiorella et al. | |
| 8,118,827 B2 | 2/2012 | Duerig et al. | |
| 8,298,257 B2 | 10/2012 | Sepetka et al. | |
| 8,323,243 B2 | 12/2012 | Schneider et al. | |
| 8,465,509 B2 | 6/2013 | Shekalim | |
| 8,475,487 B2 | 7/2013 | Bonnette et al. | |
| 8,646,460 B2 | 2/2014 | Utley et al. | |
| 8,657,867 B2 | 2/2014 | Dorn et al. | |
| 8,734,465 B2 | 5/2014 | Teague | |
| 8,795,305 B2 | 8/2014 | Martin et al. | |
| 8,795,322 B2 | 8/2014 | Cully et al. | |
| 8,801,748 B2 | 8/2014 | Martin | |
| 8,936,583 B2 * | 1/2015 | Holzbauer | A61F 5/441 604/326 |
| 9,186,487 B2 | 11/2015 | Dubrul et al. | |
| 9,408,625 B2 | 8/2016 | Remmerswaal et al. | |
| 9,451,984 B2 | 9/2016 | Zhou et al. | |
| 9,463,035 B1 | 10/2016 | Greenhalgh et al. | |
| 9,622,762 B2 | 4/2017 | Dahm et al. | |
| 9,622,770 B2 * | 4/2017 | Trapp | A61B 17/12113 |
| 9,700,350 B2 * | 7/2017 | Barker | A61N 1/0551 |
| 9,775,631 B2 | 10/2017 | Li et al. | |
| 9,826,995 B2 | 11/2017 | Dahm et al. | |
| 10,010,335 B2 | 7/2018 | Greenhalgh et al. | |
| 10,022,139 B2 | 7/2018 | Kobayashi et al. | |
| 10,028,759 B2 | 7/2018 | Wallace et al. | |
| 10,080,575 B2 | 9/2018 | Brady et al. | |
| 10,159,509 B2 | 12/2018 | Nishio et al. | |
| 10,252,036 B2 | 4/2019 | Aggerholm et al. | |
| 10,278,715 B2 | 5/2019 | Dahm et al. | |
| 10,300,256 B2 | 5/2019 | Aboytes | |
| 10,383,645 B2 | 8/2019 | Nishigishi | |
| 10,383,751 B2 | 8/2019 | Ferrera et al. | |
| 10,499,934 B2 | 12/2019 | Dahm et al. | |
| 10,653,433 B2 | 5/2020 | Masubuchi et al. | |
| 10,667,833 B2 | 6/2020 | Vale et al. | |
| 10,722,255 B2 | 7/2020 | Lenker et al. | |
| 10,743,907 B2 | 8/2020 | Bruzzi et al. | |
| 10,813,663 B2 | 10/2020 | Bruzzi et al. | |
| 10,835,269 B1 | 11/2020 | Wallace et al. | |
| 10,874,410 B2 | 12/2020 | Scarpine et al. | |
| 10,925,624 B2 | 2/2021 | Diamant et al. | |
| 11,026,709 B2 * | 6/2021 | Greenhalgh | A61B 17/22 |
| 11,364,363 B2 * | 6/2022 | Fantuzzi | A61M 25/0009 |
| 2003/0083623 A1 * | 5/2003 | Berg | A61M 25/0012 604/164.13 |
| 2005/0182387 A1 * | 8/2005 | Webler | A61M 25/0668 604/164.05 |
| 2007/0060942 A2 | 3/2007 | Zadno Azizi | |
| 2018/0042626 A1 | 2/2018 | Greenhalgh et al. | |
| 2019/0105055 A1 * | 4/2019 | Cao | A61B 17/0057 |
| 2019/0117214 A1 | 4/2019 | Harari et al. | |
| 2019/0133616 A1 | 5/2019 | Sachar et al. | |
| 2019/0133627 A1 * | 5/2019 | Wallace | A61B 17/320725 |
| 2020/0078045 A1 | 3/2020 | Wallace et al. | |
| 2020/0121336 A1 | 4/2020 | Tsukamoto et al. | |

FOREIGN PATENT DOCUMENTS

| | | | |
|---|---|---|---|
| WO | WO2018/078563 | A1 | 5/2018 |
| WO | WO2018/193597 | A1 | 10/2018 |
| WO | WO2018/193598 | A1 | 10/2018 |
| WO | WO2020/113957 | A1 | 6/2020 |
| WO | WO2020/162724 | A1 | 8/2020 |
| WO | 2021167594 | A1 | 8/2021 |

OTHER PUBLICATIONS

Deaton et al.; U.S. Appl. No. 17/519,539 entitled "Thrombectomy methods," filed Nov. 4, 2021.

International Search Report and Written Opinion dated May 3, 2022 for International Application No. PCT/US2022/016690.

* cited by examiner

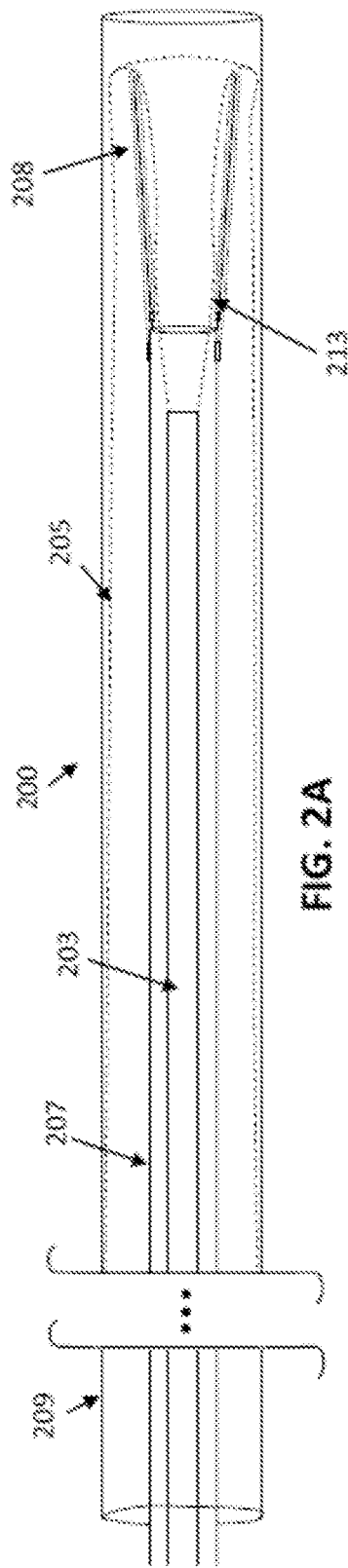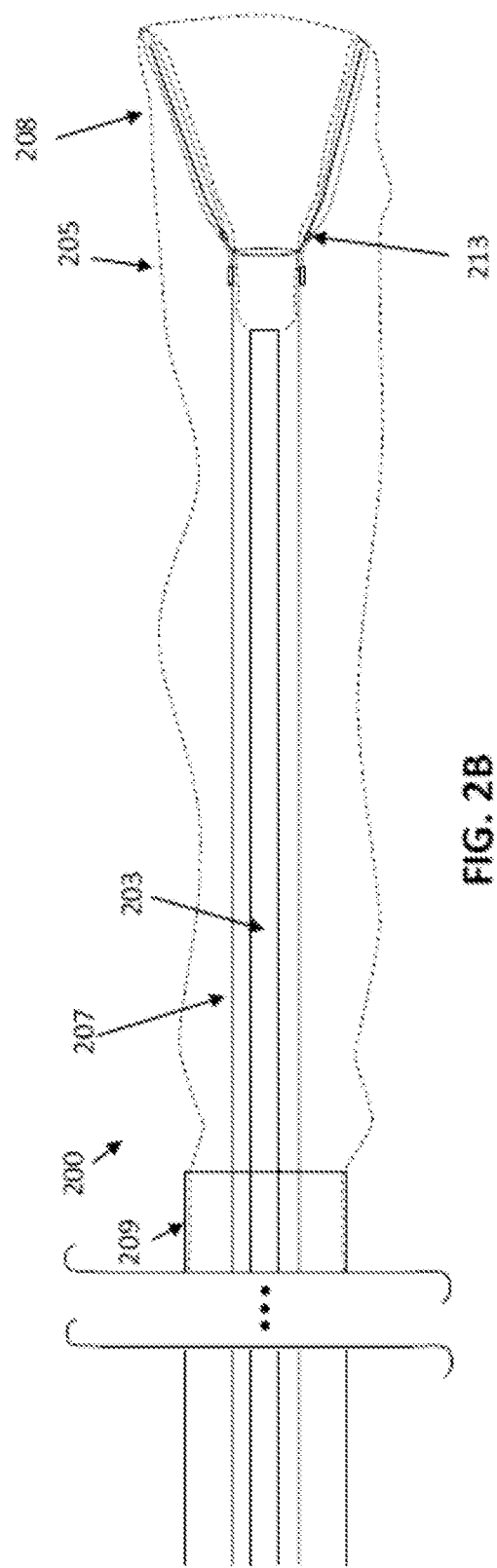
FIG. 2A
FIG. 2B

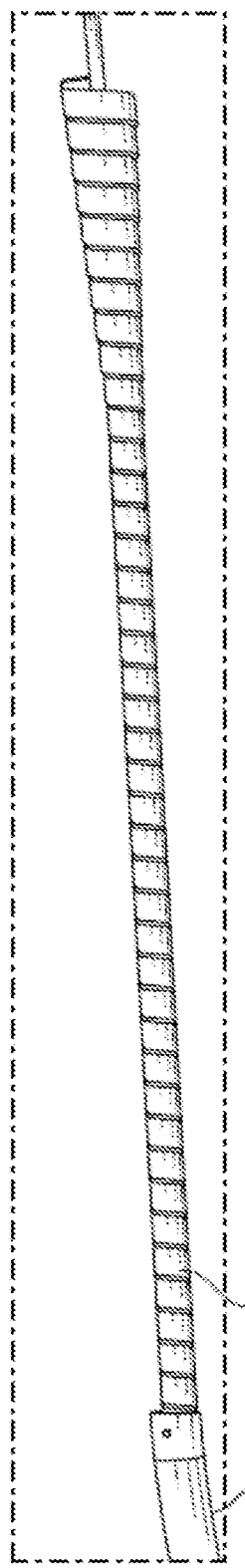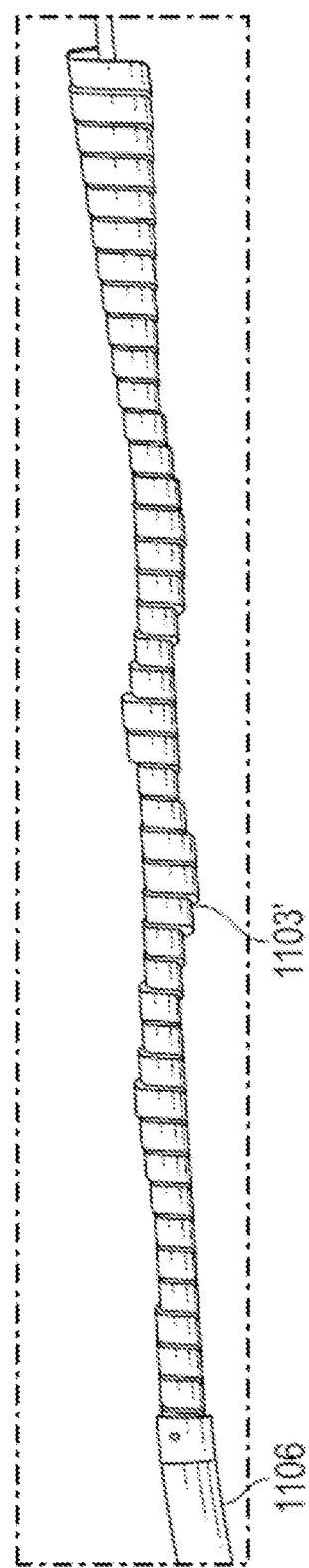

THROMBECTOMY APPARATUSES AND METHODS

CROSS REFERENCE TO RELATED APPLICATIONS

This patent application claims priority to U.S. Provisional Patent Application No. 63/151,054, titled "THROMBECTOMY TOOLS AND APPARATUSES" and filed on Feb. 18, 2021, and to U.S. Provisional Patent Application No. 63/249,561, titled "THROMBECTOMY TOOLS AND APPARATUSES" and filed on Sep. 28, 2021, each of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

Removal of material from within a vessel or chamber is often useful. For example, removal of tissue such as blood clots from within a vasculature may improve patient conditions and quality of life. Clot removal may be beneficial or even necessary to improve patient outcomes. For example, in the peripheral vasculature, interventions and procedures can reduce the need for an amputation by 80 percent. The ultimate goal of any technique to treat these conditions is to remove the blockage and to restore patency, quickly, safely, and cost effectively.

Devices for mechanically removing material, including thrombus material, from with a lumen of the vessel may include an inverting tube for removing material from a body lumen, such as for removing a clot from a blood vessel (e.g., thrombectomy devices), are disclosed and described in each of U.S. Pat. No. 10,271,864, as well as in each of U.S. Patent Application Publication Nos. 2019/0117214, 2018/0042626 and 2018/0042624, and in U.S. patent application Ser. No. 16/566,393. These apparatuses do an excellent job at removing material from within a blood vessel, but in some situations may face challenges when removing large amounts of material which may require multiple attempts to remove, and/or when removing softer clot material, which may be difficult to grip. In some cases, it may be difficult to completely remove clot material from against the wall of the vessel.

Thus, there is a need for devices, including thrombectomy devices, that can remove tissue, and particularly large and/or soft materials, from within a body lumen. Described herein are apparatuses (devices, systems and kit) and methods of using them that may address the needs and problems discussed above.

SUMMARY OF THE DISCLOSURE

The methods and apparatuses (devices, systems, etc.) described herein relate to improvement in the operation, and in particular, the insertion and use of, materials for removing material from within a vessel. These methods and apparatuses may include inverting tube apparatuses for removing material from within a body, including a body lumen. These apparatuses may generally include an inversion support, which may include a catheter ("inversion support catheter") and a flexible tube configured to move over the outside of the inversion support and invert into the inversion support. In some examples a puller attached to a first end of the inversion support for pulling the flexible tube into the inversion support. In some examples the inversion support includes a funnel region at its distal end that may be collapsible and expandable and may be biased to expand into an expanded funnel shape. The apparatuses described herein may be generally referred to as apparatuses for removing a material from a vessel and may be configured as mechanical thrombectomy apparatuses.

The methods and apparatuses described herein may provide improvements for introducing inverting tube apparatuses into the body, including in particular introduces for inserting inverting tube apparatuses including an expandable funnel at the distal end region of the apparatus.

The methods and apparatuses described herein may include methods and apparatuses (e.g., systems, devices, etc.) for loading a second (or additional) flexible tube onto an inversion support that has already been used. Also described herein are system and methods for assisting in accurately, quickly, and cleanly (e.g., within a sterile field) loading a flexible tube onto an inversion support catheter so that it may be redeployed within the lumen of a vessel to remove additional material.

Alternatively or additionally, described herein are methods and apparatuses for reloading a flexible tube that has already been partially or completely used, over and onto the inversion support so that it can be reused.

Also described herein are methods and apparatuses for assisting in removal of material (e.g., clot material), including removing clot material from the vessel wall(s). These methods and apparatuses may be used by themselves or in conjunction with (and as part of) a system for removing clot material by inverting (rolling) a flexible tube into an inversion support catheter.

For example, described herein are introducers for coupling a flexible tube of an inverting thrombectomy device to an inversion support catheter and inserting the assembled device into a sheath hub. An introducer apparatuses may include: a flexible knitted or woven tube; a puller coupled to one end of the knitted or woven tube; an outer cover extending over the knitted or woven tube; an inner cover extending at least partially within a lumen of the knitted or woven tube; and a handle portion continuous with the outer cover and the inner cover, wherein the handle portion comprise a frangible region that is configured to be broken along a predetermine tear line extending through the handle, the inner cover and the outer cover so that the handle portion, inner cover and outer cover may be peeled away from the flexible knitted or woven tube after breaking the frangible region.

The outer cover may comprise a distal end configured to mate with a sheath hub so that the flexible knitted or woven tube may be driven out of the introducer apparatus and into the sheath hub.

The distal end may comprise a mating engagement configured to mate with the sheath hub. The handle portion may comprise an opening though the handle portion that is continuous with the lumen of the knitted or woven tube. The apparatus may include a second tear line extending from the frangible portion through both the outer cover and the inner cover. The tear line may extend from a proximal end to a distal end of the device, wherein the handle portion is on the proximal end of the device.

The handle portion may be configured to be grasped by one hand. For example, the handle portion may be T-shaped. A distal end of the outer cover may be tapered. The tear line(s) may be perforated.

Also described herein are devices with enhanced clot grabbing. For example, in some cases the apparatus may include a short funnel region on the inversion support catheter and the flexible tube may comprises a knit having a long loop length. For example, an apparatus for removing a material from within a body lumen, may include: an inversion support catheter having an expandable funnel-shaped distal end, wherein the funnel shape has a length of about 0.8 cm or less; a puller within and configured to freely slide with a lumen of the inversion support catheter; and a knitted or woven flexible tube extending from a distal end region of the puller, over a distal end opening of the funnel-shaped distal end and over an outer surface of the inversion support catheter, wherein the knitted or flexible woven tube comprises interlocking loops that are longer than 2 mm or greater.

The knitted or woven flexible tube may be formed of a filament having a rectangular cross-section. The rectangular cross-section may have rounded edges. The rectangular cross-section may have a ratio of long side to short side of between about 1:2 and about 3:4. The knitted or woven flexible tube may comprise a knitted flexible tube. The funnel shape may have a length of about 0.6 cm or less (about 0.5 cm or less, etc.). The puller may be a hypotube, wire, catheter, etc.

The interlocking loops may be 3 mm or greater (e.g., 3.1 mm or greater, 3.2 mm or greater, 3.3 mm or greater, 3.4 mm or greater, 3.5 mm or greater, 3.6 mm or greater, 3.7 mm or greater, 3.8 mm or greater, 3.9 mm or greater, 4 mm or greater, etc.).

The knitted or woven flexible tube over a distal end of the inversion support catheter may be arranged so that adjacent interlocking loops are at least partially stacked on top of each other.

Also described herein are apparatus for removing a material from within a body lumen comprising: an inversion support catheter having an inner lumen and an outer surface; a puller within the inner lumen and configured to freely slide with the inner lumen; and a co-knit flexible tube extending from a distal end region of the puller, over a distal end opening of the funnel-shaped distal end and over an outer surface of the inversion support catheter, wherein the co-knit flexible tube comprises a pair of adjacent filaments that are co-knit to form a plurality of interlocking loops, wherein the apparatus is configured so that pulling the puller proximally causes the interlocking loops of the co-knit flexible tube to roll and invert over a distal end opening of the inversion support catheter from the outer surface and into the inner lumen.

The inversion support catheter may include an expandable funnel-shaped distal end.

The first filaments of the pair of filaments forming the co-knit flexible tube may be different from the second filament of the pair of filaments forming the co-knit flexible tube, or the same. In some examples the first filament comprises a rectangular cross-section. The second filament may include a stainless steel filament. The first filament may comprise a Nitinol filament.

Also described herein are methods of reusing the flexible tube of the inverting thrombectomy apparatuses described herein. For example a method of reloading a flexible tube of an inverting thrombectomy apparatus after a flexible tube of the inverting thrombectomy apparatus has been inverted and withdrawn at least partially into an inversion support catheter of the inverting thrombectomy apparatus may include: compressing a portion of the flexible tube that is within the inversion support catheter so that loops of the flexible tube are at least partially stacked within the inversion support catheter, wherein an internal support extends through the flexible tube and inversion support catheter; and securing the inversion support catheter relative to the flexible tube and pulling a free end of the flexible tube that is on an outer surface of the inversion support catheter proximally so that the inversion support catheter rolls out and inverts over a distal end of the inversion support catheter.

Compressing may comprises securing a distal end region of the support wire and pulling the free end of the flexible tube while allowing the inversion support catheter to slide proximally over the internal support.

The internal support may comprise an internal support wire.

Securing may comprise manually pinning the distal end region. Securing the inversion support catheter may comprise manually pining the inversion support catheter. Securing the inversion support catheter may comprise preventing the inversion support catheter from sliding proximally by a stop on the internal support.

Any of these methods may include inserting the internal support through a lumen within the flexible tube passing through the inversion support catheter. Pulling the free end of the flexible tube may comprise gripping a cuff region on the free end of the flexible tube.

The cuff region may be configured to prevent the free end from inverting into the inner lumen of the inversion support catheter.

Any of these methods may include washing the flexible tube to remove clot material from the flexible tube and/or reinserting the inverting thrombectomy apparatus into a patient's body.

All of the methods and apparatuses described herein, in any combination, are herein contemplated and can be used to achieve the benefits as described herein.

BRIEF DESCRIPTION OF THE DRAWINGS

A better understanding of the features and advantages of the methods and apparatuses described herein will be obtained by reference to the following detailed description that sets forth illustrative examples, and the accompanying drawings of which:

In FIG. 1A, the assembled apparatus is shown in a side view, showing an inversion support catheter and a flexible outer tube. FIG. 1B shows the inverting tube apparatus of FIG. 1A in a vessel, proximal to a clot. FIG. 1C illustrates the removal of a clot from the vessel using the apparatus of FIG. 1A, by pulling the flexible tube on the outside of the inversion support catheter proximally so that it rolls over the distal end of the inversion support catheter and into the inversion support catheter, drawing the clot with it; the apparatus may be advanced distally.

FIGS. 2A-2B illustrate another example of an inverting tube apparatus including an expandable funnel that is attached to distal end of the inversion support catheter. FIG. 2B shows the inverting tube apparatus of FIG. 2A in a deployed configuration with an intermediate (e.g., delivery)

catheter withdrawn proximally so that the expandable funnel at the distal end of the inversion support catheter can expand.

Figure 3A:
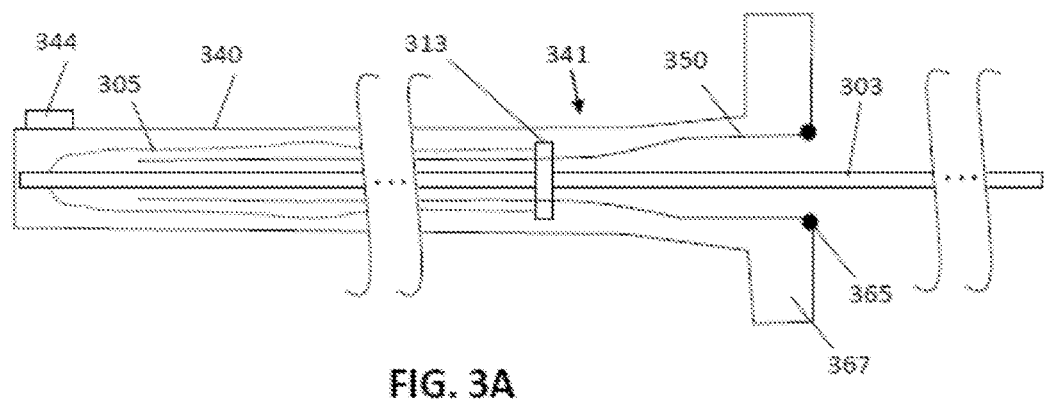
Figure 3B:
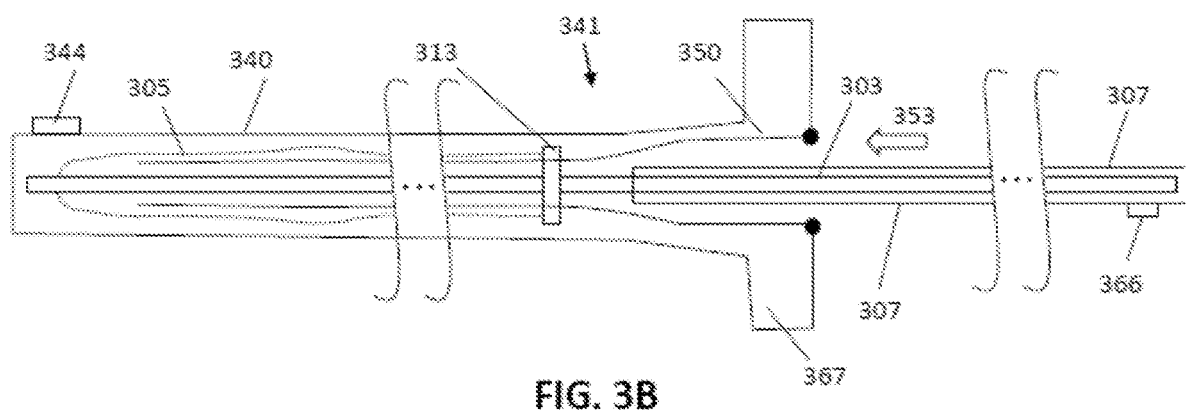
Figure 3C:
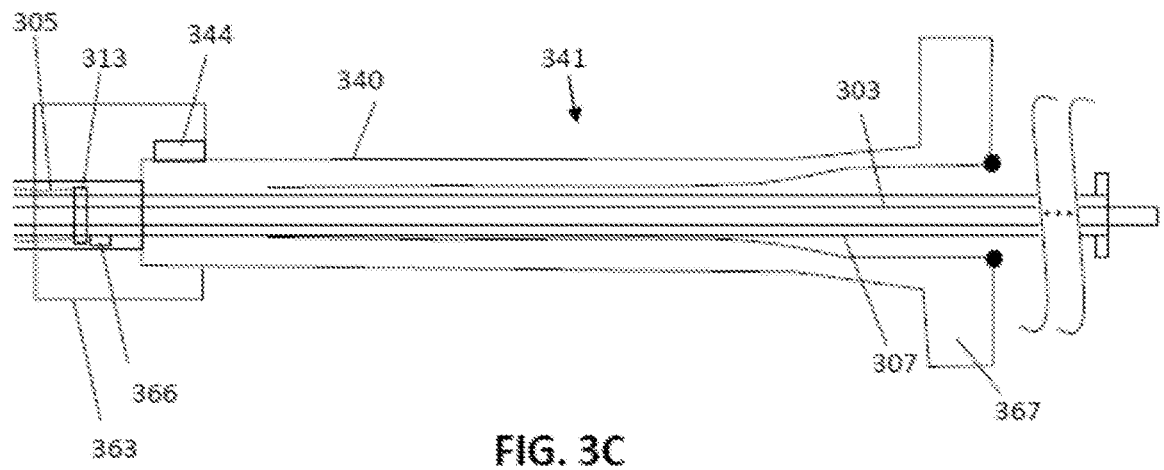
Figure 3D:
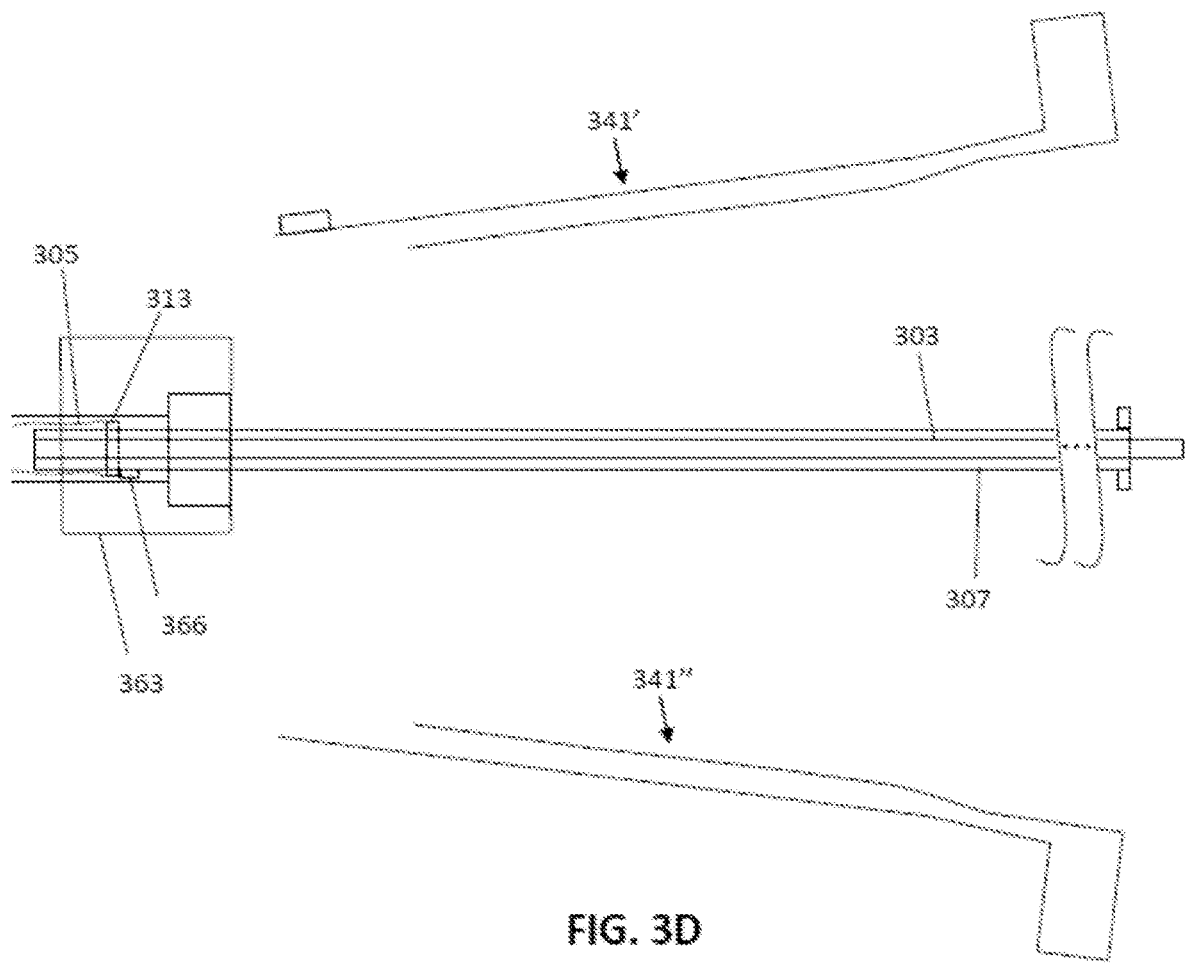

FIGS. 3A-3D illustrate one example of an introducer for a flexible tube (e.g., tractor) for loading an inversion support catheter and for introducing into the sheath hub for positioning in the body. FIG. 3A shows an introducing having an outer and inner cover protecting a flexible tube within the tear-away introducer. FIG. 3B illustrates the loading of an inversion support into the introducer of FIG. 3A to position the flexible tube over the inversion support catheter. FIG. 3C shows the introducer of FIG. 3A with the flexible tube loaded onto the inversion support catheter and positioned into the sheath hub. FIG. 3D shows the tear-away introducer being removed for positioning and operating the inverting thrombectomy apparatus with the flexible tube loaded onto the inversion support catheter.

Figure 4A:
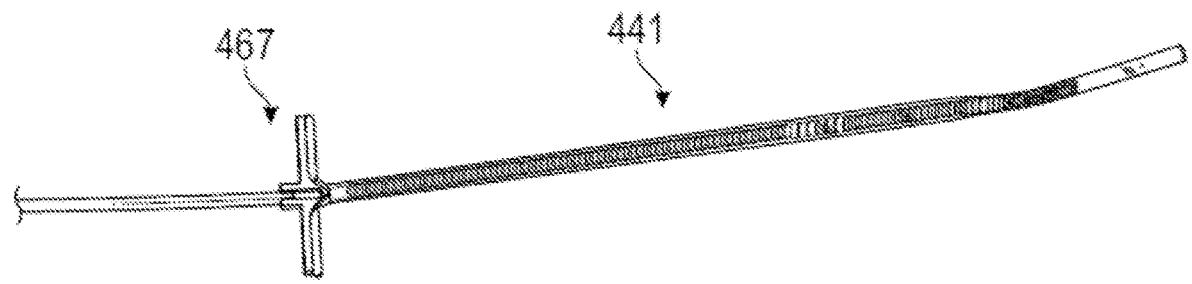
Figure 4B:
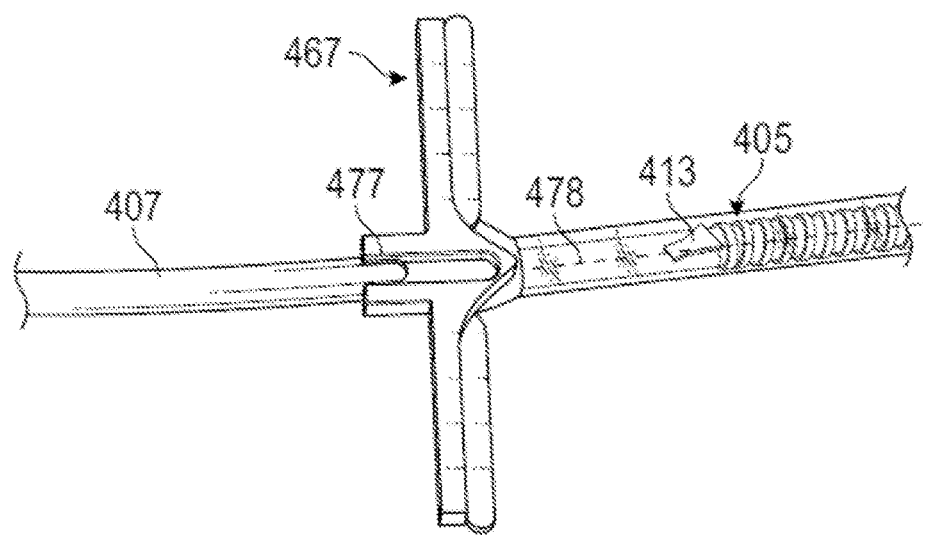
Figure 4C:
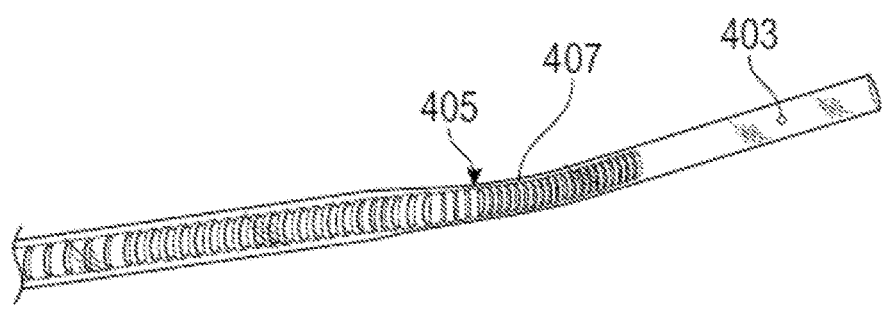

FIGS. 4A-4C illustrate one example of an introducer similar to that shown in FIGS. 3A-3D, including a breakaway handle and inner and outer cover.

Figure 5A:
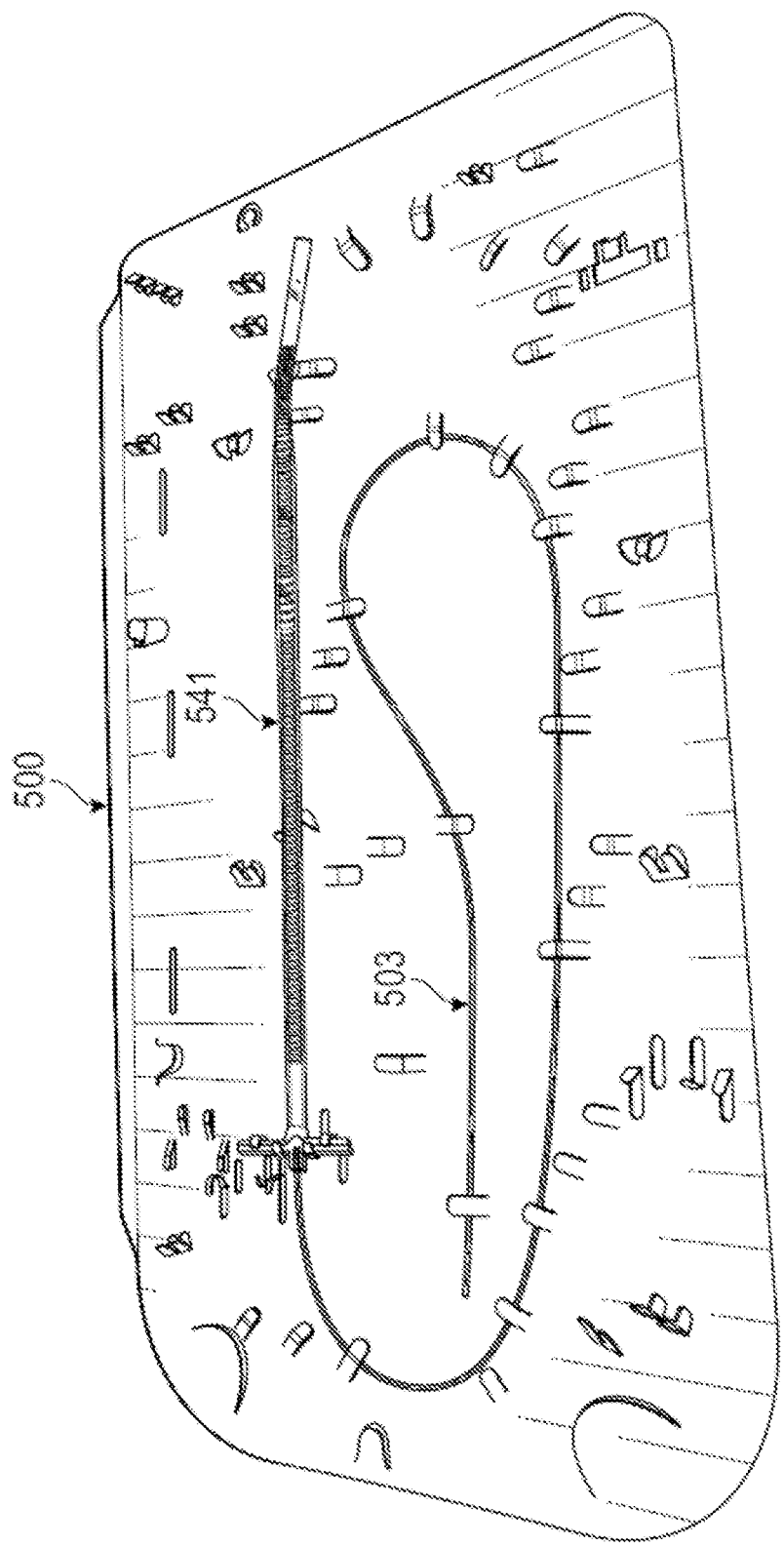
Figure 5B:
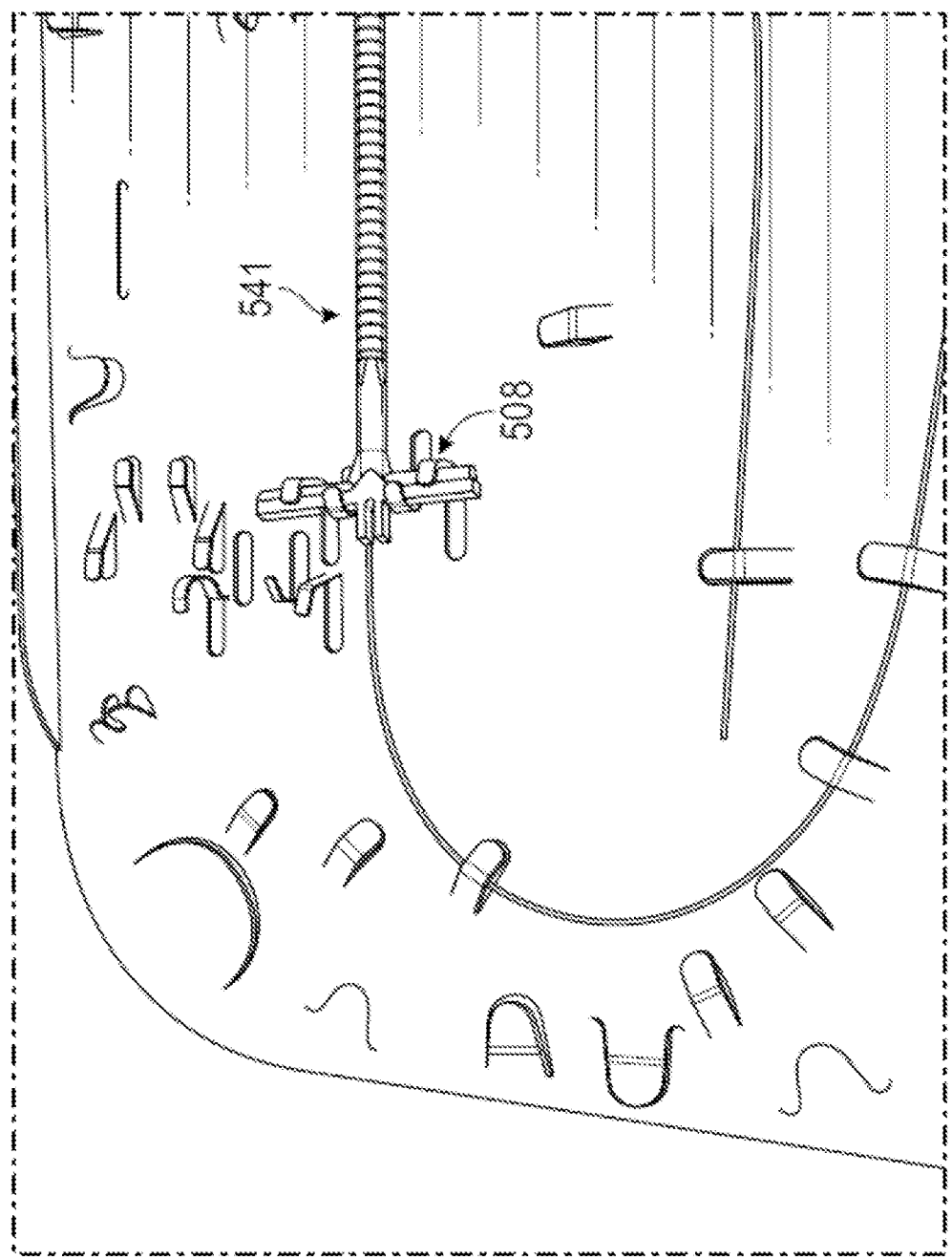

FIGS. 5A and 5B illustrate one example of a jig/mount for loading and preparing an introducer similar to that shown in FIGS. 3A-3D.

Figure 6A:
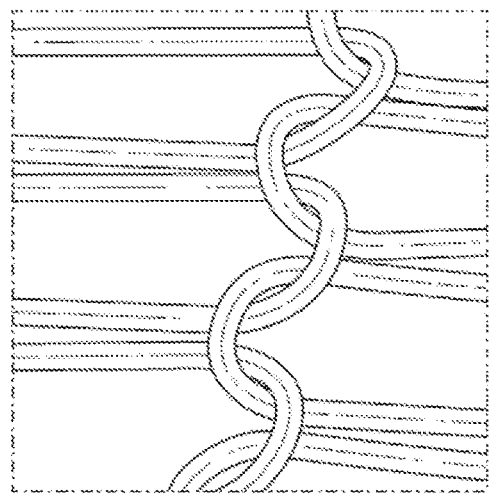
Figure 6B:
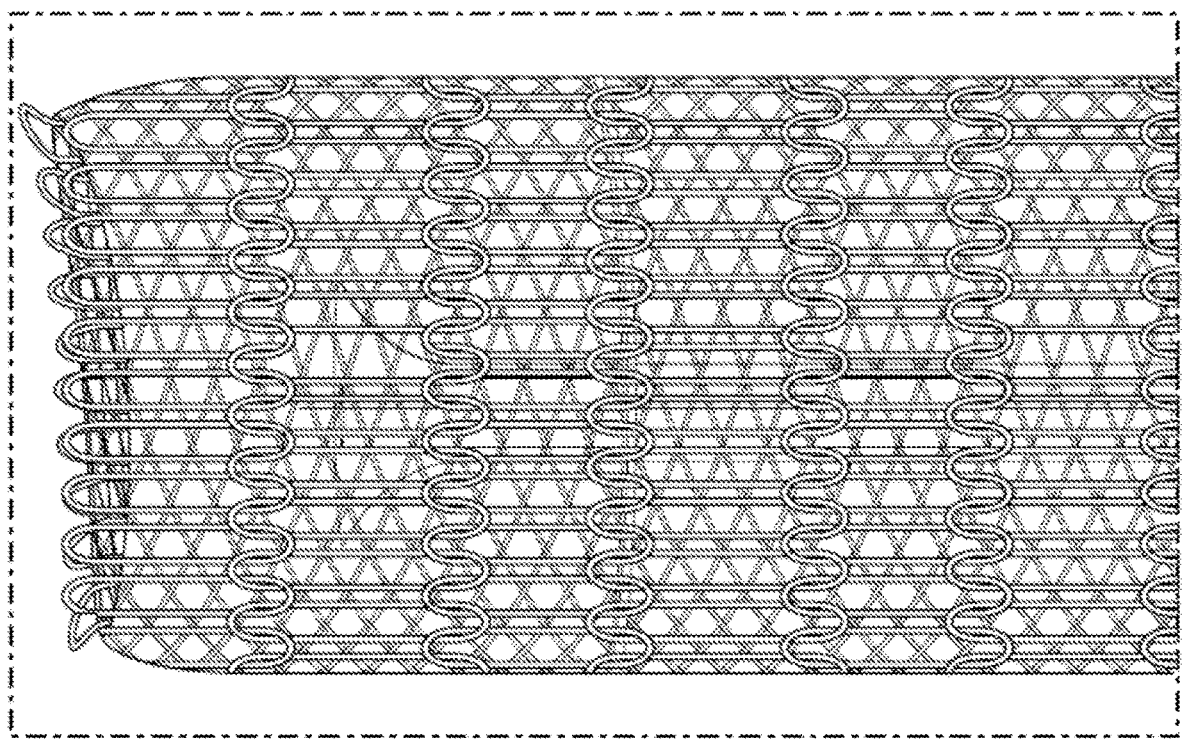

FIGS. 6A and 6B show examples of filaments having oval cross-sections for forming a knitted (or in some examples, woven or braided) flexible tube.

Figure 7:
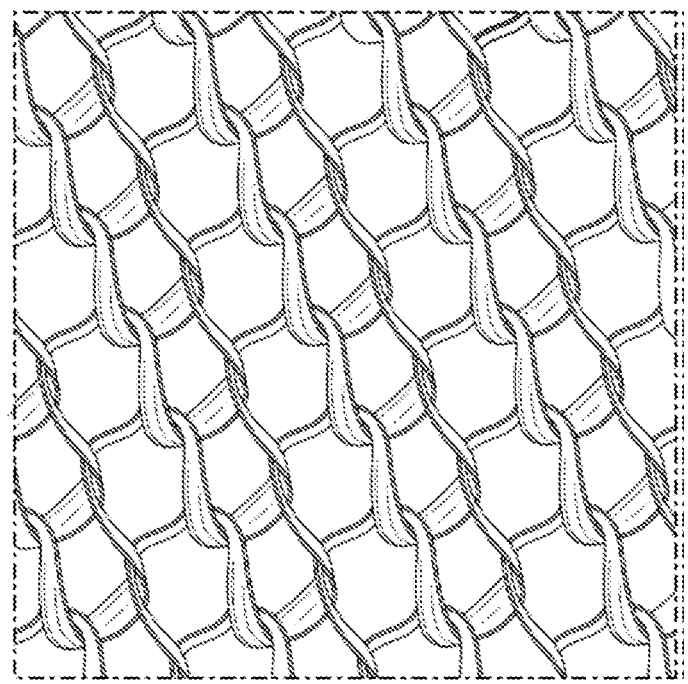

FIG. 7 shows an example of a filament having a flattened cross-section.

Figure 8A:
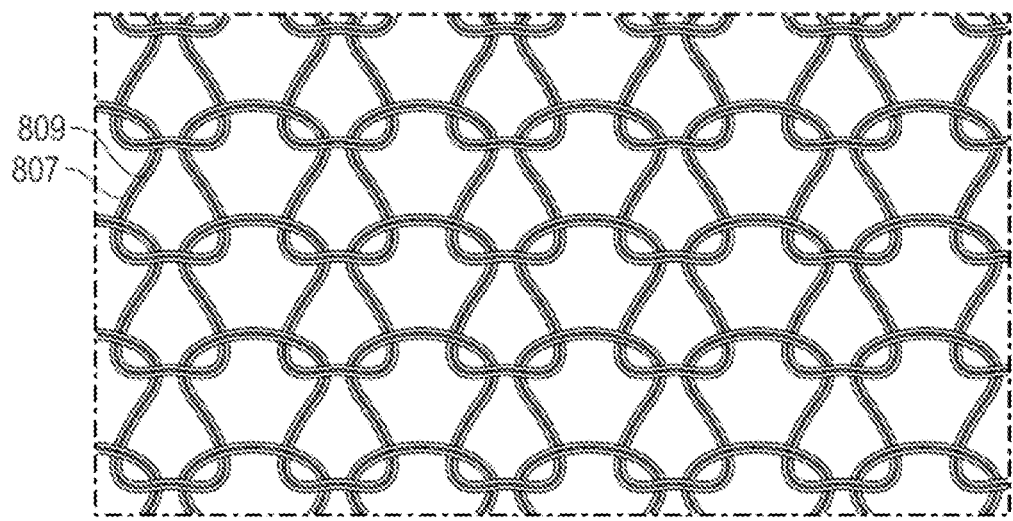
Figure 8B:
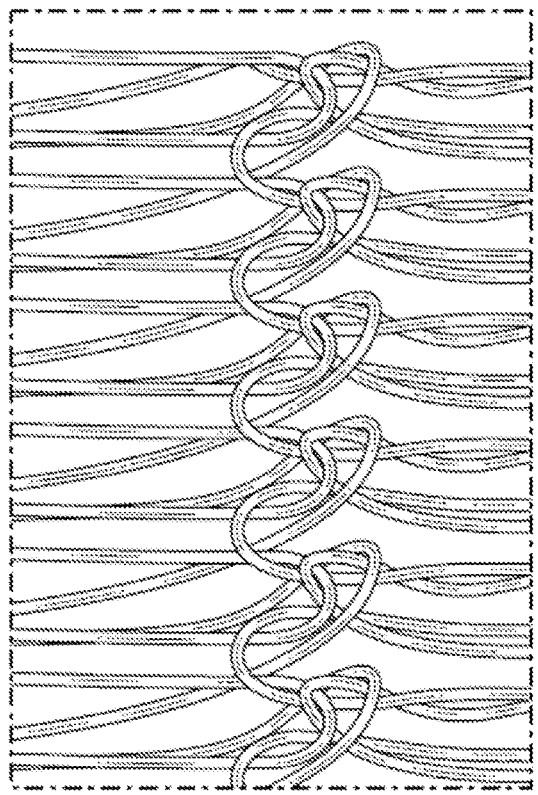
Figure 8C:
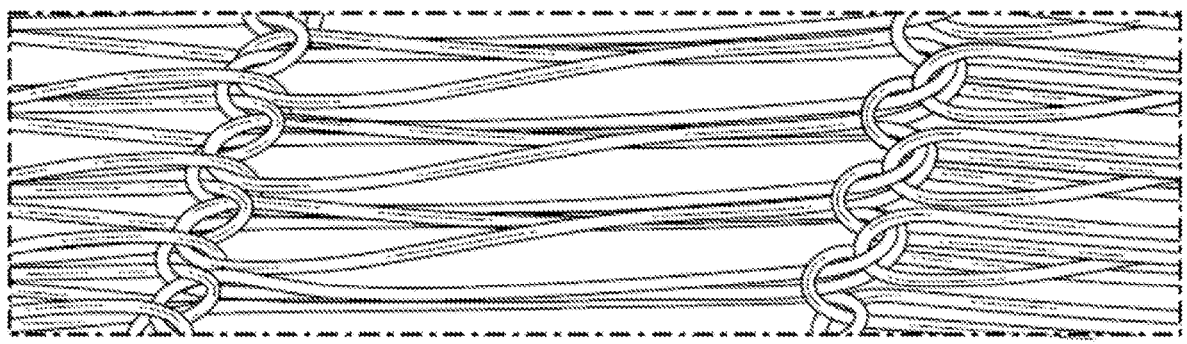

FIG. 8A-8C show examples of kitted flexible tube formed by co-knitted filaments (two filaments in this example). FIG. 8A shows the knitted material formed by co-knitting two or more filaments. FIGS. 8B and 8C show knuckle regions of the co-knit flexible tube material shown in FIG. 8A.

Figure 9:
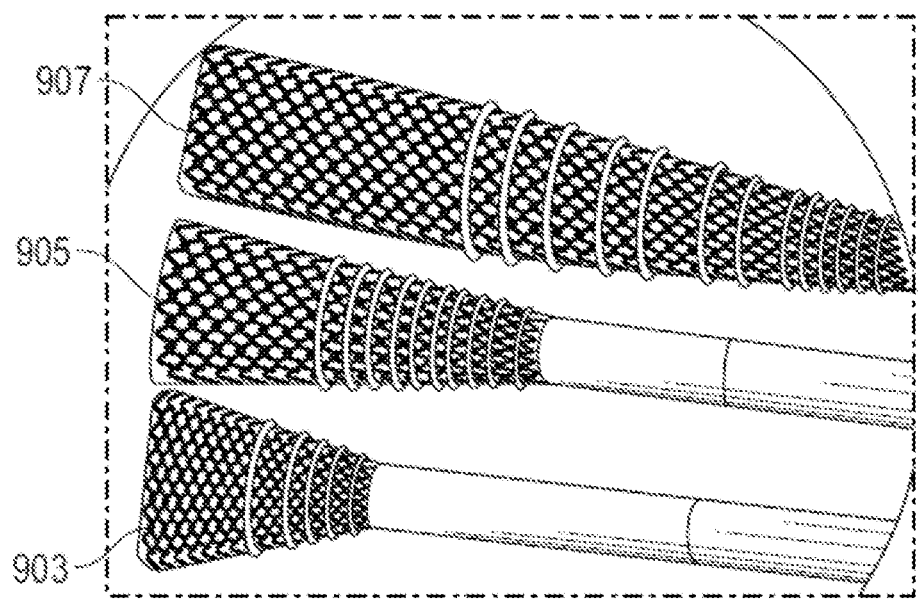

FIG. 9 illustrates three examples of funnel regions having different lengths (from the base of the funnel to the tip of the expandable funnel region.

Figure 10:
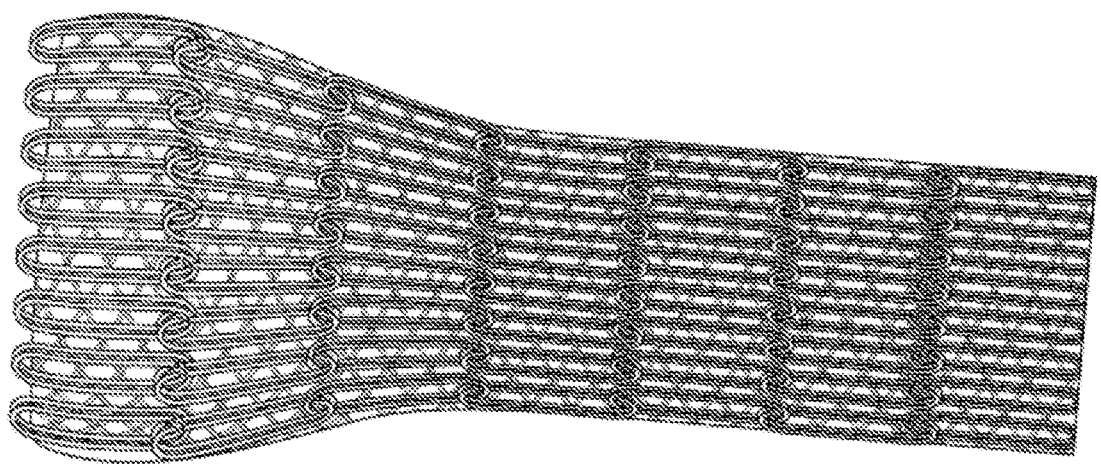

FIG. 10 illustrates an example of a portion of an inverting thrombectomy apparatus having a short (e.g., <0.6 cm) length of the funnel and relatively long loops of the knit material.

FIGS. 11A-11B illustrate one method of using fluid pressure to provide slack to the portion of the flexible tube over the distal end region of the inversion support catheter.

Figure 12A:
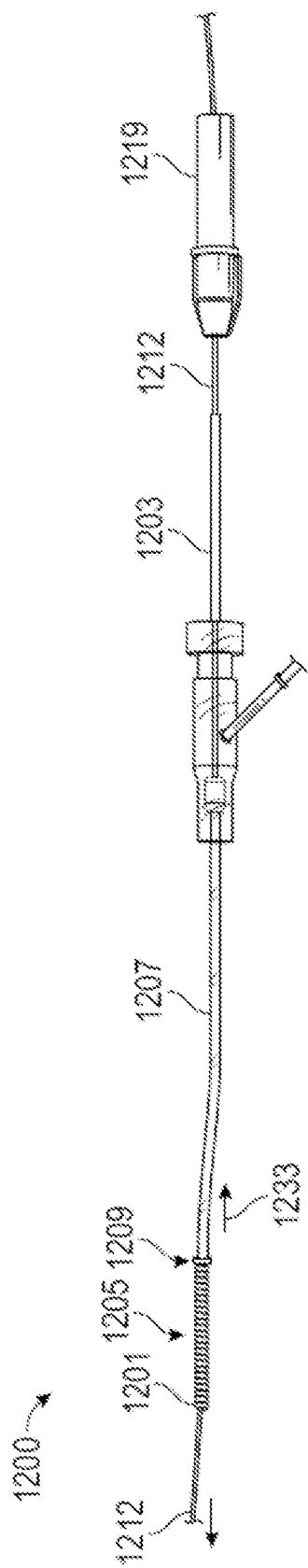
Figure 12B:
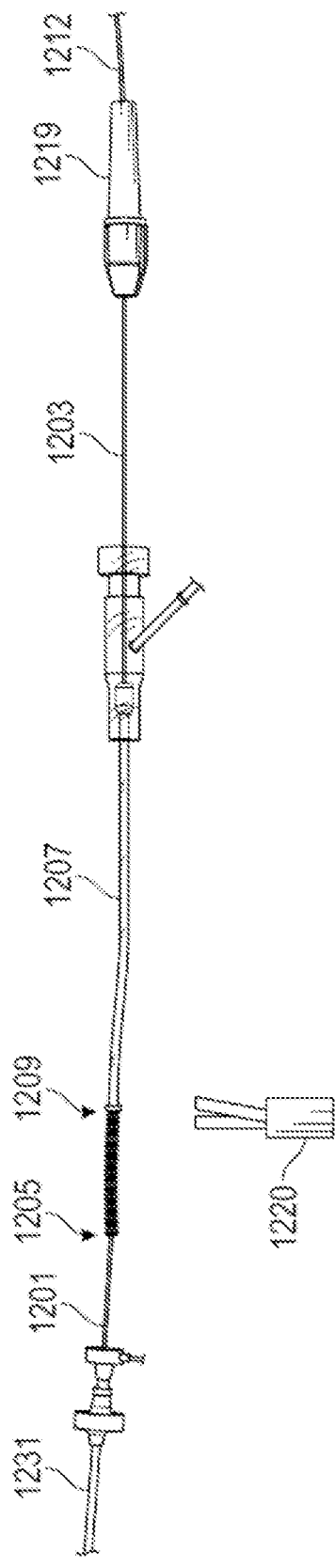

FIGS. 12A-12B illustrate examples of inverting tube apparatuses in which the flexible tube may be reset and reused for removing material (e.g., clot) from within the body. In FIG. 12B the inverting tube apparatus may include a manipulating member for grasping the cuff region of the flexible tube, as described herein.

Figure 13:
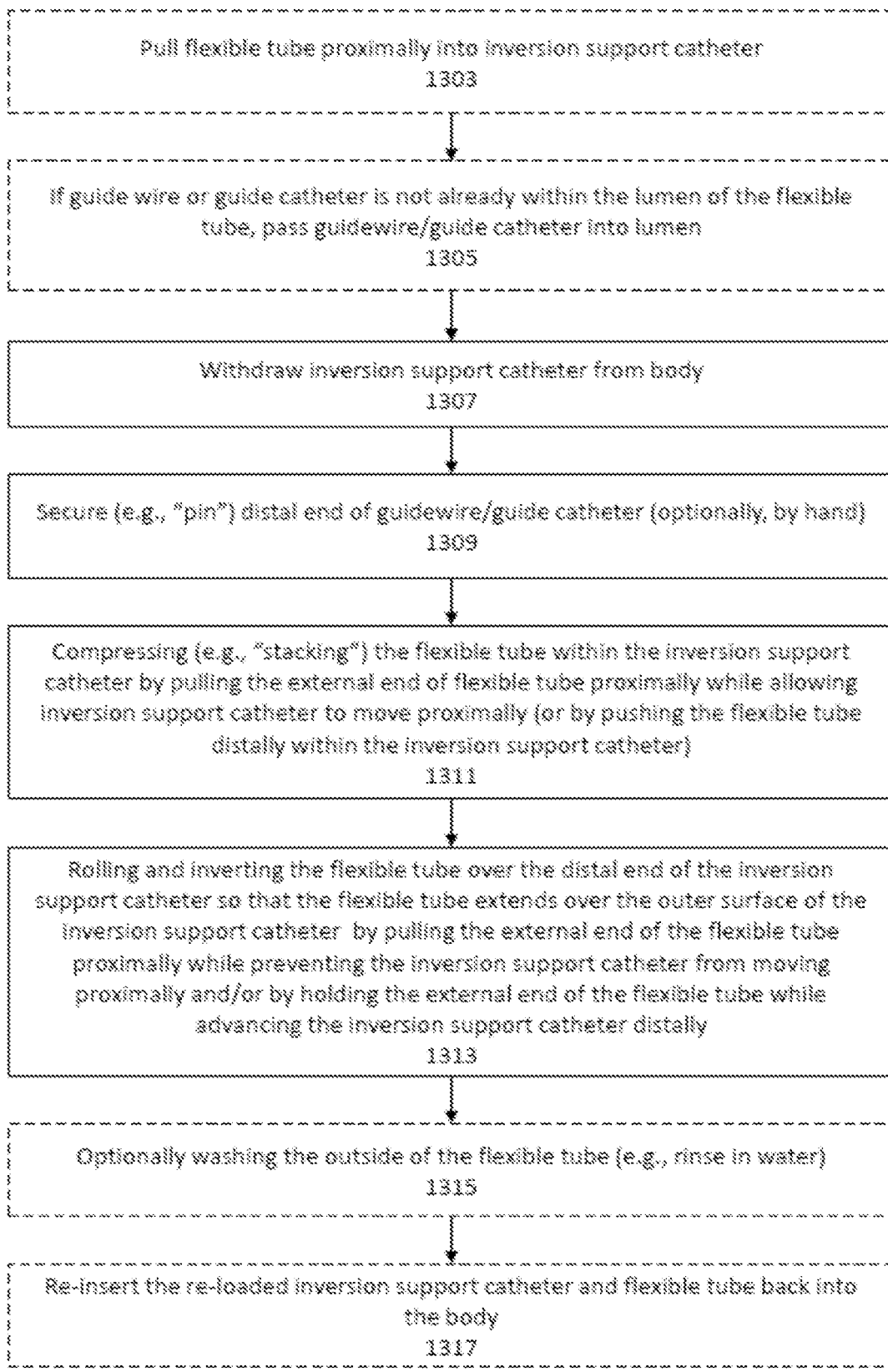

FIG. 13 illustrates one example of a method of resetting (and/or reusing) a flexible tube of an inverting tube apparatuses as described herein.

FIGS. 14A-14E illustrate an example of a method of resetting (and/or reusing) a flexible tube of an inverting tube apparatuses as described herein.

FIGS. 15A-15H illustrate a method of operating an inverting tube apparatus, including resetting and reusing the flexible tube of the inverting tube apparatus after it has been used at least once for collecting clot material.

FIGS. 16A-16F illustrate an example of a method of resetting (and/or reusing) a flexible tube of an inverting tube apparatuses as described herein.

Figure 17A:
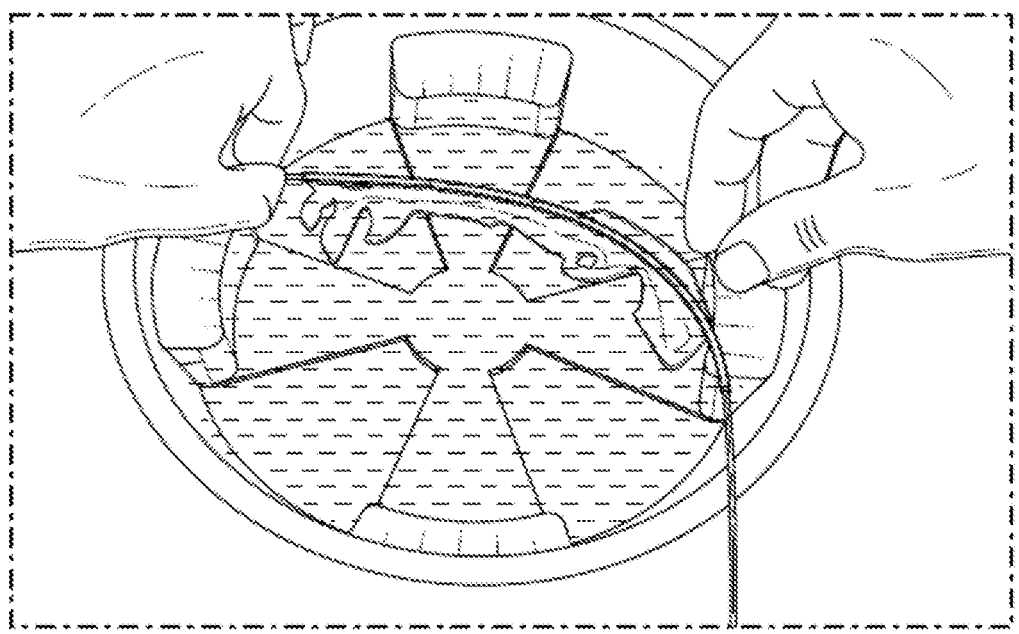
Figure 17B:
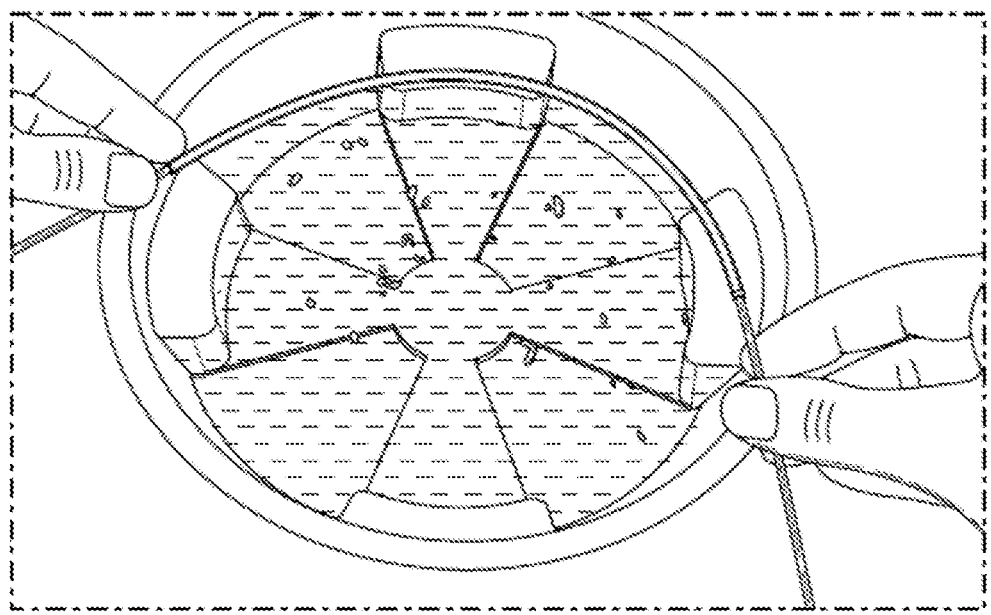

FIGS. 17A-17B show one method of washing a reset flexible tube of an inverting tube apparatuses as described herein to remove material (e.g., clot).

DETAILED DESCRIPTION

The methods and apparatuses described herein may also relate to improvement in the operation, and in particular, the insertion and use of, inverting tube apparatuses for removing material from within a body. These apparatuses may generally include an inversion support, which may include a catheter and in some examples a funnel region at the distal end of the catheter, a flexible tube configured to move over the outside of the inversion support and invert into the inversion support, and in some examples a puller attached to a first end of the inversion support for pulling the flexible tube into the inversion support. These apparatuses may be generally referred to as apparatuses for removing a material from a vessel and may be configured as mechanical thrombectomy apparatuses.

The methods and apparatuses described herein may provide improvements for introducing inverting tube apparatuses into the body, including in particular methods and apparatuses for loading (or in some cases reloading) a flexible tube portion onto an inversion support catheter. This may allow the re-use of the same inversion support catheter, and in some cases the re-use of the same flexible tube with the same (or a different) inversion support catheter. The assembled apparatus (inversion support catheter and flexible tube) may then be inserted back into the body lumen (e.g., vessel lumen). Also described herein are systems that may assist the user in reloading and/or reusing the flexible tube (or a new flexible tube) onto an inversion support catheter and reinserting it into the body.

Also described herein are systems and methods for improving the ability of the flexible tube to grab material from the walls of the body lumen. Also described herein are methods for enhancing or improving the ability of the apparatus to grab clot by creating slack into the flexible tube before it inverts over the distal end of the inversion support catheter.

Any of these features, components and techniques may be used separately or in combination.

For example, described herein are apparatuses (e.g., systems) including one or more introducers for introducing an inverting tube apparatus into a sheath, or a hub of a sheath, so that they may be delivered into the body for deployment and operation. Any of these apparatuses may include an introducer that is configured to enable low-friction introduction of an apparatus including an expandable distal funnel (e.g., as part of the inversion support) into the body. The introducer may be removed, e.g., by peeling away the introducer once the device is loaded into the hub or sheath, as will be described in greater detail herein. As described herein, multiple peal-away protective regions may be concurrently removed from over and within the flexible tube to allow the flexible tube to be applied over the inversion support catheter so that it can be inserted (through the introducer) into the body, including (optionally) over a guidewire or guide catheter.

In general, the apparatuses may be configured to be inserted into the body via a sheath so that the apparatus can be delivered, using a deployment cannula and/or guidewire, to the target region of the body. In examples in which the apparatus includes a funnel it may be otherwise difficult to transfer the expandable funnel portion of the apparatus into the sheath and therefore into the body. A standard introducer at the back of a sheath (e.g., sheath hub) may require large amounts of force in order to insert the portion of the apparatus including the expandable funnel; this force may result in partially or wholly collapsing and/or jamming the apparatus. For example, if the introducer is pushed in too hard or far into the sheath hub, the tip of the introducer may at least partially collapse circumferentially, pinching/grabbing the inversion support, e.g., at the funnel tip region, making it hard to transfer the inversion support into the sheath. Further, if the introducer is not pushed far enough into the sheath hub, this may result in a dead space that may make it hard to transfer the apparatus (e.g., the inversion support) into the sheath.

Described herein are apparatuses, introducer apparatuses that are configured to easily and cleanly collapse the expandable funnel portion of an inversion support and control the insertion depth of the introducer into the sheath hub. These introducers may also be configured as peel-away introducers and may include a stop element to guide how far the introducer may be inserted into sheath hub. In particular, as mentioned, these apparatuses may be configured as dual peal-away devices that may concurrently remove both inner and outer introducers, making them much easier to use.

Figure 1A:
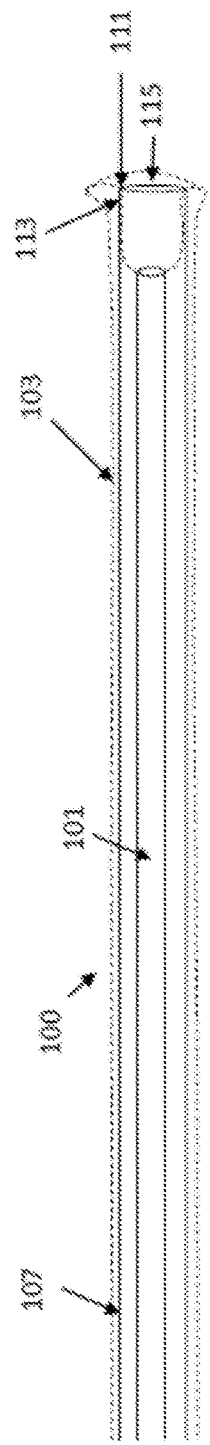
FIGS. 1A-1C illustrate an example of an inverting tube (e.g., thrombectomy) apparatus that may be used to remove material from a vessel.
Figure 1B:
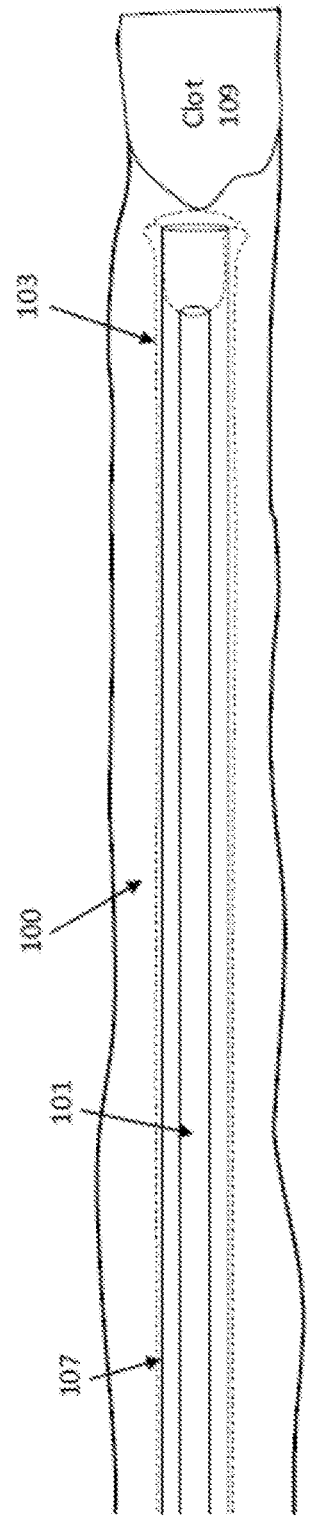
Figure 1C:
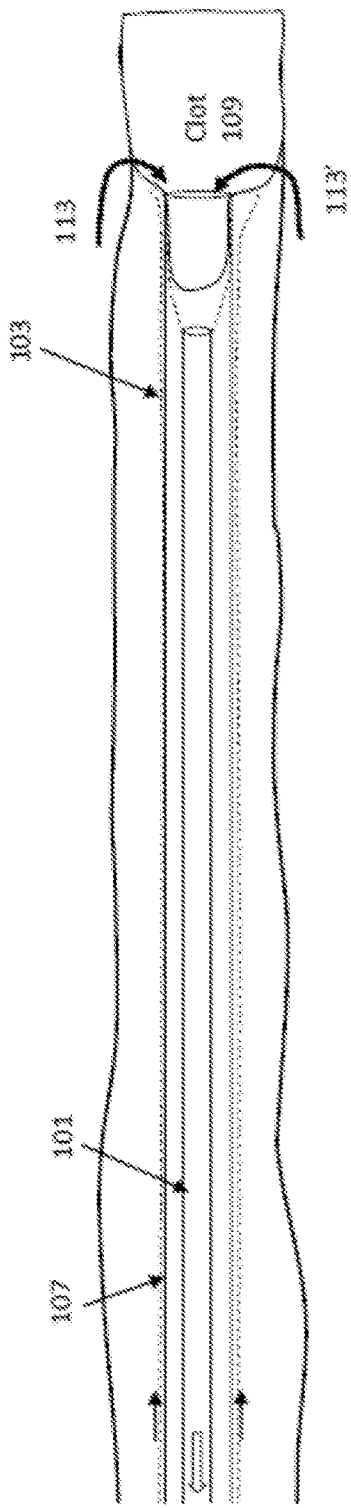

In general, an inverting tube apparatus (also referred to herein as "mechanical thrombectomy apparatus" or "inverting thrombectomy apparatus") may be configured to remove material, such as clot, using a length of inverting tube, as shown in FIGS. 1A-1C. The apparatuses and methods of using them described herein may be used within the vasculature, including the neurovasculature and the peripheral vasculature.

For example, FIG. 1A illustrates an example of an inverting thrombectomy apparatus 100, such as described in U.S. patent application Ser. No. 15/496,570, and in U.S. Pat. No. 9,463,035. The apparatus includes an inversion support catheter 107 and a flexible tube 103 that extends over the outer surface of the inversion catheter. The flexible tube may be referred to as a tractor tube (or flexible tractor tube) and may be attached at one end region to a puller 101, which may be pull wire or pull tube (e.g., catheter), e.g., at the distal end region of the puller. In some examples the flexible tube may be attached proximal to the distal end of the puller (e.g. between 1 mm and 50 mm from the distal end, between 1 mm and 40 mm, between 1 mm and 30 mm, greater than 5 mm, greater than 10 mm, greater than 20 mm, greater than 30 mm, etc. from the distal end of the puller). Pulling the puller proximally inverts the flexible tube over the distal end opening 111 of the inversion support catheter to capture and remove a material (such as a clot) in the vessel lumen, as shown in FIGS. 1B and 1C. In operation, the amount of the material that may be captured corresponds to the length of the flexible tube.

In FIG. 1B the inverting tractor mechanical thrombectomy apparatus 100 is shown deployed near a clot 109. In the deployed configuration the puller 101 (shown here as a puller micro catheter, alternatively the puller may be a wire) is held within an elongate inversion support catheter 107 so that the flexile tractor tube 103 extends from the end of the puller 101 and expands toward the inner radius of the elongate inversion support catheter 107; at the distal end opening 111 of the elongate inversion support catheter the tractor tube inverts over itself and extends proximally in an inverted configuration over the distal end of the elongate inversion support catheter. As shown in FIG. 1C, by pulling the puller proximally, the tractor tube rolls 113, 113' and everts over the distal end opening of the elongate inversion support catheter, drawing the adjacent clot into the elongate inversion support catheter, as shown.

FIG. 1A the elongate inversion support catheter is an elongate tube having a distal end that has the same size inner diameter as the proximal length of the inversion support catheter. In some examples the distal end 115 of the inversion support catheter may be funnel-shaped (or configured to expand into a funnel shape, see, e.g. FIGS. 2A-2B). In FIGS. 1A-1C, the inversion support catheter 107 is shown positioned between the tractor tube (e.g., flexible tube 103) and the puller 101 so that the flexible tube can be pulled proximally by pulling on the puller and rolling the flexible tube into the elongate inversion support catheter so that it inverts. The portion of the flexible tube that is inverted over the distal end 115 of the elongate inversion support catheter has an outer diameter that is greater than the outer diameter of the elongate inversion support catheter. The flexible tube may be biased so that it has a relaxed expanded configuration with a diameter that is greater than the outer diameter (OD) of the elongate inversion support catheter; in addition, the flexible tube may also be configured (e.g., by heat setting, etc.) so that when the flexible tube is everted and rolled over the distal end opening into the elongate inversion support catheter, the outer diameter of the flexible tube within the elongate inversion support catheter has an outer diameter that is about y times (y fold) the inner diameter of the elongate inversion support catheter (e.g., where y is greater than 0.1×, 0.5×, 0.6×, 0.7×, 0.75×, 0.8×, 0.9×, 1×, etc. the inner diameter, ID, of the elongate inversion support catheter. This combination of an un-inverted diameter of the flexible tube of greater than the diameter of the OD of the elongate inversion support catheter and an inverted diameter of the flexible tube of greater than, e.g., 0.7× the ID of the elongate inversion support catheter is surprisingly helpful for preventing jamming of the apparatus, both when deploying the apparatus and when rolling the flexible tube over the distal end opening of the elongate inversion support catheter to grab a clot. The flexible tube may be expandable and may be coupled to the puller as shown. In some examples the flexible tube and the puller may comprise the same material, but the flexible tube may be more flexible and/or expandable, or may be connected to elongate puller (e.g., a push/pull wire or catheter). As mentioned above, the puller may be optional (e.g., the flexible tube may itself be pulled proximally into the inversion support catheter).

In FIG. 1C the clot may be drawn into the elongate inversion support catheter by pulling the flexible tube proximally into the distal end of the elongate inversion support catheter, as indicated by the arrows 113, 113' showing pulling of the inner portion of the flexible tube, resulting in rolling the flexible tube over the end opening of the catheter and into the catheter distal end and inverting the expandable distal end region so that it is pulled into the catheter, shown by arrows. The end of the flexible tube outside of the catheter may be loose relative to the outer wall of the catheter.

2A-2B illustrate an example of an inverting tube apparatus that includes a funnel region at the distal end of an inversion support catheter. In this example the inverting tube apparatus 200 includes an elongate, flexible inversion support catheter 207 that has an expandable funnel 208 at the distal end, shown in a collapsed configuration in FIG. 2A within an intermediate (e.g., delivery) catheter 209, and in an open configuration in FIG. 2B after being released from the intermediate catheter. The funnel may be formed of a woven material and may be porous, particularly at the base region 213, where the funnel extends from the body of the elongate body of the inversion support catheter. A flexible tube 205 extends over the distal end (including the funnel) of the inversion support catheter and inverts over the distal opening of the funnel. The flexible tube may be, e.g., a knitted material, and may be biased to expand to an outer diameter (OD) that is larger than the OD of the funnel 208 in the open configuration. The flexible tube is attached to a distal end region of a puller 203. The flexible tube (e.g., "tractor") is attached to the distal end region of the puller. The funnel may include two or more regions having different wall angles.

The apparatuses shown in FIGS. 1A-1C and 2A-2B may be modified or used with any of the methods and apparatuses described herein.

Improvements in the reloading and packaging (including packaging configured to assist in reloading) of these apparatuses are also described herein. In general, a flexible tube portion of the apparatus may be configured as a replacement or additional flexible tube ("tractor") that may be used to reload onto an inversion support catheter of an apparatus. These supplemental (e.g., reloading or replacement) tractors may be preassembled with two or more peel-away covers.

Also described herein are peel-away introducers for replacement flexible tubes (tractors) for any of the apparatuses described herein. In some examples, the peel-away introducer may be configured with a handle at the proximal end that is frangible (or that includes a frangible region) so that it may be removed after loading the inversion support catheter and driving the loaded inversion support catheter (loaded with the flexible tube) into the hub (e.g., sheath) and therefore into an introducer sheath and/or catheter within the patient. These introducers are substantially easier to use and operate for both reloading and for inserting into the patient, while maintaining the sterility of the apparatus.

FIGS. 3A-3C illustrate one example of an improved dual peel-away introducer. In FIG. 3A, the flexible tube (tractor) is preloaded into the dual peel-away introducer. The peel-away introducer is configured as a dual peel-away introducer because it includes both an outer protective cover (introducer 340) and an inner protective cover 350. The outer protective cover may be rigid or semi-rigid and may protect the flexible tube from being touched. In some examples the flexible tube may be held in a stacked and/or compressed configuration within the introducer. In some examples (not shown) a wire or tube (e.g., guidewire, guide catheter and/or stylet) may present or inserted within the inner lumen of the tractor to provide additional support when loading onto an inversion support catheter and/or inserting into the patient through a hub (sheath). For example, in some examples it may be beneficial to cover all or most of the outside of the flexible tube with a cover (introducer 340) to prevent manual contact that may interfere with the tractor.

For example, any of the apparatuses (e.g., systems) described herein may include an introducer (e.g., "cover") as shown in FIG. 3A, for covering all or a portion of a flexible tube. As mentioned, the introducer may also be configured to hold the tractor in a compressed configuration.

The dual peel-away introducer shown in FIG. 3A includes a replacement or secondary flexible tube 305 (tractor) that may be loaded onto/with an inversion support and may then be inserted into a patient body lumen, e.g., through a hub 363 (or sheath) and into a sheath. In this example, the outer surface 340 of the introducer 341 may be long, e.g., long enough to cover the majority of the length of the tractor; the tractor 305 is per-positioned within the introducer and may be coupled at one end to a puller 303 (e.g., at a distal end region of the puller 303). The puller may be a catheter (e.g., microcatheter). As shown, the flexible tube within the introducer may extend proximally over the puller 303 but between the outer surface of the introducer and an inner introducer surface 350.

The cover/introducer 341 shown in FIGS. 3A-3C is a dual tear-away cover/introducer and includes a proximal handle 367 having an end region 365. The handle portion is separatable into two or more pieces, and each piece may be connected to different portions of the outer cover and to different portion of the inner cover, so that separating the handle into these different parts peels apart the outer cover and inner cover (each into two or more pieces). The handle may be frangible (breakable in a predetermined line or region). For example, both the inner cover and the outer cover may include one or more tear lines extending down the distal-to-proximal length of the device (not shown).

The outer cover 340 of the introducer 341 may also include an insertion stop 344 at the proximal end region to limit how far into the hub (e.g., into a sheath) the introducer may be inserted. In some examples the inversion support catheter may include a funnel at the distal end (as shown in FIGS. 2A-2B, above).

The inner cover 340 may be positioned between all or a portion of the tractor 305 and the puller 303 within the introducer; this inner cover 350 or sleeve may help in loading the inversion support onto/into the flexible tube within the introducer, as illustrated in FIG. 3B. The second cover region of the introducer 350 may be referred to as an inner cover (or inner cheater) and may also be a peel-away cover, e.g., having one or more tear away lines or regions that may extend partially or completely down the length of the inner introducer. The tear lines define a predetermined region that may be separated to remove the introducer after loading the assembled inversion support catheter and flexible tube into a hub/sheath.

For example, in FIG. 3B, an inversion support 307 is inserted 353 over the puller 303 that extends from the introducer 341 and is connected near the distal end to the flexible tube 305 within the introducer. The inner cover 350 may help guide the inversion support 307 into the connector without interfering with the flexible tube, as shown in FIGS. 3B-3C. In FIG. 3B, the inversion support (inversion support catheter) may be inserted partially or completely, until the distal end of the inversion support is at the distal end region of the flexible tube. In some examples a stop or catch 366 on an outer surface of the inversion support may engage with a proximal end (a loose or free proximal end) of the flexible tube 313. This end of the flexible tube may be configured as a collar region with a material (e.g., a polymeric material) that increases the stiffness of the collar region of the flexible tube. In some examples, this collar region may include slits or regions that allow it to invert over the distal end of the inversion support when the flexible tube is pulled into the inversion support to grab material (e.g., clot) as described above. Alternatively, in some examples this collar region 313 is configured to prevent the proximal end from inverting over the distal end of the inversion support.

FIG. 3C shows an example of the introducer 341 of FIG. 3B in which the inversion support 307 is fully loaded into the introducer, and the loaded introducer is attached to a hub (e.g., sheath hub) 363 that is coupled to the patient (not shown). The introducer may lock into the sheath hub when the insertion stop 344 engages with the sheath hub, as shown in FIG. 3C. The assembly of the inversion support and flexible tube may then be advanced distally into the patient within the sheath by advancing the inversion support (and in some cases the puller, which may be actively or passively advanced) distally. In FIG. 3C, the assembly of the inversion support, flexible tube and puller has been advanced distally until the loose end of the flexible tube (including the cuff 313) is within the sheath hub, 363, as shown. Thereafter, the introducer 341 may be broken apart and separated away from the assembly, as shown in FIG. 3D.

As mentioned, the handle, outer cover and inner cover may be separated (e.g., by tearing, peeling, etc., such as by tearing it along its length) so that the introducer may be removed without interfering with the insertion of the assembly. As shown in FIG. 3D the separated portions of the introducer 341', 341" may be removed and disposed of, leaving the mechanical thrombectomy apparatus (the inversion support, flexible tube and puller) to be positioned, in some cases over a guidewire or guide catheter (not shown), within the body to remove material from the body.

Other improvements to the packaging may also be used to simplify and assist in operating these apparatuses, including in inserting them into the body (e.g., into a sheath hub) more easily while maintaining sterility.

FIGS. 4A-4C illustrate one example of an introducer as described above. FIG. 4A illustrates an introducer 441 that includes an outer cover and an inner cover, and a handle 467. The handle is frangible and configured to be broken apart into two pieces that are each attached to separate portions of the inner and outer covers; pulling them apart may also tear the inner and outer covers in a predetermined region (e.g., tear line) along the length of the introducer, so that it can be separated and removed from the assembled inversion support, flexible tube (e.g., tractor) and puller, as just discussed. The handle also provides one-handed support and operation of the introducer so that it can be engaged with the sheath hub and easily manipulated by the user.

FIG. 4B shows an enlarged view of the handle portion of the introducer device, showing a pair of wings that are connected by a frangible region 477 that is continuous with the tear lines 478 on the outer cover (e.g., a perforation, crease, etc.) and inner cover. In FIG. 4B a flexible tube, shown in this example as a knitted tube 405 is visible within the introducer; the proximal end of the flexible tube includes a cuff region 413. In FIGS. 4A-4C an inversion support 407 has been inserted fully into the introducer 441.

FIG. 4C shows a distal end region of the introducer, in which the flexible tube 405 is arranged over the distal end of the inversion support catheter 407. The inversion support catheter in this example includes an expandable funnel region over which the flexible tube inverts and is pulled into by pulling on the puller 403 once the device is deployed into the body.

Any of the introducers described herein may include a cover (e.g., plug, cap, etc.) at the distal end that may protect the flexible tube and/or inversion support until it is coupled to the sheath hub. In some examples the cover (e.g., plug, cap, etc.) is configured as a plunger of a syringe. An example is show in FIG. 5A.

The apparatuses described herein may include a system incorporating any of the described features and elements. For example, any of the apparatuses and methods described herein may include a jig or holder for the introducer and/or for a replacement flexible tube. The jig or holder may include fasteners for releasably holding the introducer and the elongate body of the puller and/or the elongate body of the inversion support. In some cases the jig or holder may be formed from the packaging.

For example, FIG. 5A illustrates one example of a jig or holder 500 that is configured to releasably hold an introducer 541 that is preloaded with a flexible tube coupled to a puller 503. The puller includes an elongate body that extends distally from the introducer. In FIG. 5A the jig or holder is a sheet of polymeric material that includes claps (pre-formed as cut out tabs in the sheet) that are bent and are oriented so that the introducer is held securely by tabs 508 that face each other (see, e.g., FIG. 5B, showing the facing tabs 508 holding the handle region of the introducer). The jig/hold is also configured with tabs that are arranged so that they hold the puller in a spiral arrangement, with the cut-out ends of the tabs (all but the last one) facing into the spiral. This arrangement holds the puller securely but allows it to be removed by pulling in a single direction. The last tab (closest to the proximal end of the puller) is reversed, and faces the opposite direction, which may prevent the puller from accidentally coming loose.

The jig/holder may also include one or more tabs for securing other components of the assembly, including the inversion support.

In use, the distal end of the elongate inversion support may be fed over the puller (and in some cases over a guidewire, guide catheter and/or stylet within the puller) so that it may be inserted into the introducer as described above. The distal end region of the inversion support may be attached to the jig/holder as the proximal end (which may also be held within a separate applicator, which may also be a tear-away inversion support introducer) of the inversion support inserted into the introducer.

The jig/holder may assist the user in managing the otherwise unwieldy lengths of the puller and inversion support. Since these structures must be maintained within the sterile field, it is important that they be managed while minimizing the risk that they will become contaminated. In any of the methods and apparatuses describe herein, the jig/holder may be part of the (e.g., sterile) packaging. The jig/holder may be configured as a tray, so that one or more edges (e.g., the long edge(s)) are turned upwards to prevent rolling or sliding off of the jig/holder.

Apparatuses for Capturing Soft Clot

Any of the apparatuses described herein may be adapted to capture soft material, such as soft clots, that may otherwise be difficult to capture. For example, described herein are apparatuses in which the flexible tube is a knit or woven tube that is formed of a filament that is optimized for capturing softer materials. Soft materials, such as soft clots, may be particularly difficult to capture where there is a back tension on the flexible tube, resisting the force pulling the flexible tube over the distal end opening of the inversion support (e.g., inversion support catheter) and into the inversion support.

For example in some examples the flexible tube is formed of a filament having a more rectangular cross-section, such as a wire of dimensions 0.002"×0.003", as shown in FIGS. 6A and 6B. In FIG. 6A, the filament forming the knitted flexible tube is a ribbon wire having a 0.002"×0.003" dimension. FIG. 6B illustrates an example of a flexible tube inverted over a distal end (showing a funnel-shaped distal end in this example) of an inversion support catheter. Such ribbon-shaped wires (e.g., 0.0015"×0.003", 0.002"×0.004", etc.) may grab soft clot better than flexible tubes formed of round wire, both with and without back tension. Surprisingly flexible tubes formed of a knit of 0.002"×0.003" ribbon wire is also effective for capturing hard clots and is even as effective as round wire (e.g., with stitch lengths of less than about 0.180", such as about 0.120" stitch length, e.g., stitch lengths of between about 0.07" and about 0.150", between about 0.07" and about 0.14", between about 0.07" and about 0.130", etc.).

Kitted flexible tubes (e.g., "tractors") formed of other ribbon shaped materials may work, in particular, knitted flexible tubes formed of a filament that has an approximately rectangular cross section having a ratio of sides that is between about 1:2 and about 3:4 (e.g., about 2:3). Such cross-sections were superior to even substantially flat ribbons (e.g., FIG. 7). Although the cross-section is generally rectangular, the edges may be rounded (e.g., radiused).

Surprisingly knitted flexible tubes that are formed of two side-by-side filaments, as shown in FIG. 8, showing a knit of two co-knitted strands 807, 809. Flexible tubes formed of co-knitted strands were particularly effective for capturing soft clot, without significantly impacting the flexibility and ability of the flexible tube to roll over the distal end of the inversion support and into the inversion support device. More than two (e.g., 3 or more, 4 or more, etc.) co-knitted filaments may be used to form the knitted flexible tube. For example, FIGS. 8B-8C illustrate knits formed of two co-knitted filaments. In FIG. 8B, the "knuckle" region of a knitted flexible tube, where loops of co-knit filament engage with each other, are shown. The larger profile of this knuckle region may result in greater gripping for softer clot material. FIG. 8C shows another region of a knitted flexible tube formed by co-knitting two filaments of material. In FIG. 8A both co-knitted filaments are round-diameter (e.g. 0.003") stainless steel wire. Different materials (e.g., nitinol, stainless steel, etc.) may be used. For example, FIGS. 8B and 8C illustrate co-knit flexible tubes in which the filaments are different. Once filament is 0.002"×0.003" Nitinol while the second filament is 0.002" (round) Elgiloy (stainless steel).

In examples of apparatuses in which the inversion support (e.g., inversion support catheter) includes a funnel, such as an expandable funnel, at the distal end, apparatuses with funnels of shorter lengths (e.g., less than about 2.0 cm, less than about 1.75 cm, less than about 1.5 cm, less than about 1.25 cm, less than about 1.0 cm, less than about 0.9 cm, less than about 0.8 cm, less than about 0.7 cm, etc.) may be better at grabbing material (e.g., clot) than other apparatuses. For example, FIG. 9 shows three example funnel shapes. A long funnel length shape 907 (e.g., >2 cm) is shown on top, while a shorter funnel length 905 (e.g., approximately 1.2 cm length) is shown in the middle, while the shorter funnel length 903 (approximately 0.6 cm funnel length) is shown on the bottom. In some examples the shorter funnel lengths (e.g., less than 2 cm, such as less than 1.75 cm, less than 1.5 cm, less than 1.25 cm, less than 1.0 cm, less than 0.75 cm, etc.) were surprisingly and particularly effective at grabbing clot, perhaps because they produced more articulation of the "fingers" of the knitted flexible tubes.

Combination of shorter funnel (e.g., <2 cm, e.g., between 1 cm and 2.5 cm, between 1 cm and 2 cm, between 1 cm and 1.5 cm, etc.) and longer stitch length (e.g., greater than about 0.08", greater than about 0.09", greater than about 0.1", between 0.08" and 1.5", between 0.08" and 1.4", etc.) were particularly and surprisingly effective for capturing soft clot material. FIG. 10 illustrates one example of an apparatus having a short funnel shape (e.g., funnel length that is 1.2 cm or less) and longer stitch (loop) length of the woven flexible tube (e.g., greater than about 0.1"). In FIG. 10, the apparatus shown includes a flexible tube formed of a pair of filaments that are co-knit using 24 needles (therefore 24 loops in the circumference) of 0.130" stitch length, in which the first strand is 002"×0.003" Nitinol, co-knitted with a strand of 0.002" Elgiloy. The flexible tube has a 2.75 mm inner diameter that rolls over a short funnel having a length of about 0.6 cm.

As mentioned, in some examples it is beneficial when the portion of the flexible tube on the outer surface of the inversion support, just proximal to the distal end of the inversion support, is stacked or compressed slightly, so that the flexible tube may roll off over and into the inversion support catheter without significant back tension on the flexible tube. Back tension may cause the loops (e.g., arms) of the knitted flexible tube to bend rather than fan outwards, when inverting over the distal end of the apparatus. Thus, in some examples the apparatus may secure the region of the flexible tube that is outside of the inversion support catheter so that it is "stacked" with loops compressed until the puller is pulled proximally to invert and roll the flexible tube into the inner lumen and capturing material (e.g., clot) as the arms of the loops roll around the distal end. In some cases, the apparatus may be configured to apply force to release the flexile tube (where it may be trapped between the inversion support catheter outer wall and the inner wall of a delivery (e.g., intermediate) catheter.

For example, FIGS. 11A-11B illustrate an example in which fluid pressure (e.g., fluid such as buffered saline, etc.) is applied proximally through the intermediate catheter 1106 to eject a length of the knitted flexible tube 1103. In FIG. 11B the fluid pressure drives the flexible tube 1103' so that it is partially stacked, and ready to be inverted into the body, as described above.

Re-Using Flexible Tubes

Also described herein are methods and apparatuses for reusing the flexible tube after it has been at least partially deployed, e.g., by pulling it into the inversion support. Generally, as described above, the flexible tube may be used once with an inversion support, e.g., to capture material from within a body lumen. Once inverted into the inversion support catheter, it may be difficult or impossible to withdraw the flexible tube back out of the inversion support catheter, particularly in examples in which the first end of the flexible tube (e.g., tractor) is coupled to the puller while the second end is unattached (e.g., is free to slide over the outer surface of the inversion support catheter.

FIGS. 12A and 12B illustrate examples of apparatuses that may be reset and reused by removing the apparatus from the body after the flexible tube has been at least partially inverted into the inversion support catheter. In FIG. 12A, the apparatus 1200 includes a flexible tube 1205 that is coupled at one end to a puller 1203. The puller is at least partially within the inversion support catheter 1207. The second end of the flexible tube includes a cuff region 1209 that is configured to prevent it from inverting over the distal end 1201 of the inversion support catheter and may include a gripping region. For example, the cuff region may be coated with a polymeric material that reduced its flexibility to prevent it from rolling and inverting over the inversion support catheter, or a tape or other material may be applied to the second end of the flexible tube. As mentioned above, the flexible tube may generally be a knitted, woven or braided material.

The apparatus may also include an internal support member 1212, such as a wire (e.g., guidewire, catheter, stylet, etc.). In FIG. 12A the internal support member is a stylet that is positioned within the apparatus, through a lumen of the pusher. One end of the stylet is coupled to a limiter (e.g., a wire torquer) 1219 to limit travel of the inversion support catheter proximally over the internal support member.

FIG. 12B shows another example of an apparatus including a reloadable flexible tube 1205. In this example apparatus also include a manipulating member 1220, such a forceps, clamp, handle, etc. that may be used to grab or grasp onto the cuff region 1209 of the second end of the flexible tube. The example shown in FIG. 12B also includes a sheath (e.g., a 6F sheath) 1231 into which the apparatus may be withdrawn from the body or inserted into the body.

In FIGS. 12A and 12B the apparatuses are shown withdrawn from the body after already being used to remove material, e.g., by pulling the puller 1203 proximally to invert the flexible tube over the distal end opening of the inversion support catheter 1207 and into the inversion support catheter, preferably with material (clot) from within the lumen. In some examples the majority or all of the flexible tube has been withdrawn into the inversion support catheter. The flexible tube may include the cuff region described above, preventing the second end from inverting over the distal end of the inversion support catheter. The apparatus may be operated over the internal support (e.g., guidewire, guide catheter, etc.) 1212, or the internal support may be positioned within the apparatus after removing it from the body. In FIGS. 12A and 12B the flexible tube may be a woven tube.

FIG. 13 illustrate one method of operating the apparatus to reuse the flexible tube. In general, these apparatuses (inverting tube apparatuses) may be reset for reusing the flexible tube by including an internal support member, against which the apparatus may be pinned so that the flexible tube may "stack up" within the inversion support catheter, allowing it to be pulled out of the inversion support catheter proximally without locking up, which may otherwise occur.

For example, in FIG. 13, the apparatus may be initially operated to withdraw material from within the lumen of the device. For example, the flexible tube may be pulled proximally into inversion support catheter 1303 while within the body lumen (or otherwise) so that at least some of the flexible tube (e.g., "tractor") is withdrawn into the inversion support catheter. Once used, the apparatus may be removed from the body so that it can be reset for additional use. In some examples, a large amount of clot material may be removed using the same inversion support catheter and flexible tube by repeatedly inserting the apparatus into the body, removing material by pulling the flexible tube into the inversion support catheter, then withdrawing the apparatus from the body and resetting the flexible tube and reinserting it into the body.

If a guidewire or guide catheter is not already within the lumen of the flexible tube, insert an internal support (such as a guidewire, guide catheter, or stylet) into lumen after removing it from the body 1305, so that it extends completely through the apparatus, as shown in FIGS. 12A and 12B. This may be done after or before the apparatus is withdrawn from the body 1307.

The method of resetting the flexible tube may then secure (e.g., "pin") the distal end of internal support (e.g., guidewire/guide catheter), so that it does not move relative to the inversion support catheter 1309. For example, the distal end of the internal support may be pinned by hand or secured by pinning or holding.

The portion of the flexible tube within the inversion support catheter may then by compressed, e.g., by stacking the woven links of the flexible tube, within the inversion support catheter. For example, the flexible tube may be compressed by pulling the external second end of flexible tube (e.g., a cuff region) proximally while allowing inversion support catheter to move proximally, and/or by pushing the flexible tube distally within the inversion support catheter) 1311. This is illustrated in FIG. 12A by arrow 1233. Once the flexible portion within the inversion support catheter is at least partially compressed/stacked, the flexible tube may then be pulled proximally over the distal end of the inversion support catheter so that the flexible tube rolls out of and inverts onto the distal end region of the inversion support catheter and extends over the outer surface of the inversion support catheter while preventing the inversion support catheter from moving proximally 1313. For example, the inversion support catheter may be pinned or held (by hand), or it may be prevented from sliding proximally by a proximal end of the internal support (e.g., stylet) such as by a limiter 1219. For example, the flexible tube may be pulled by pulling the external end (e.g., the cuff region) of the flexible tube proximally while preventing the inversion support catheter from moving proximally. Alternatively, in some examples the second end of the flexible tube (e.g., cuff region) may be held in place while advancing the inversion support catheter distally and allowing the puller to move freely (distally) within the inversion support catheter. This may be continued until the flexible tube is mostly or entirely inverted back out of the inversion support catheter and over the outside of the inversion support catheter. The flexible tube may then be optionally washed 1315, e.g., in sterile water, buffer, or other solution, to remove the material (e.g., clot) from the flexible tube. In some examples the clot material may be sampled for later analysis. For example, the apparatus may be submerged into a saline solution and washed.

Thereafter the apparatus may be re-inserted into the patient's body 1317, including into the same vessel or another vessel in order to continue to remove material from the body lumen.

Figure 14A:
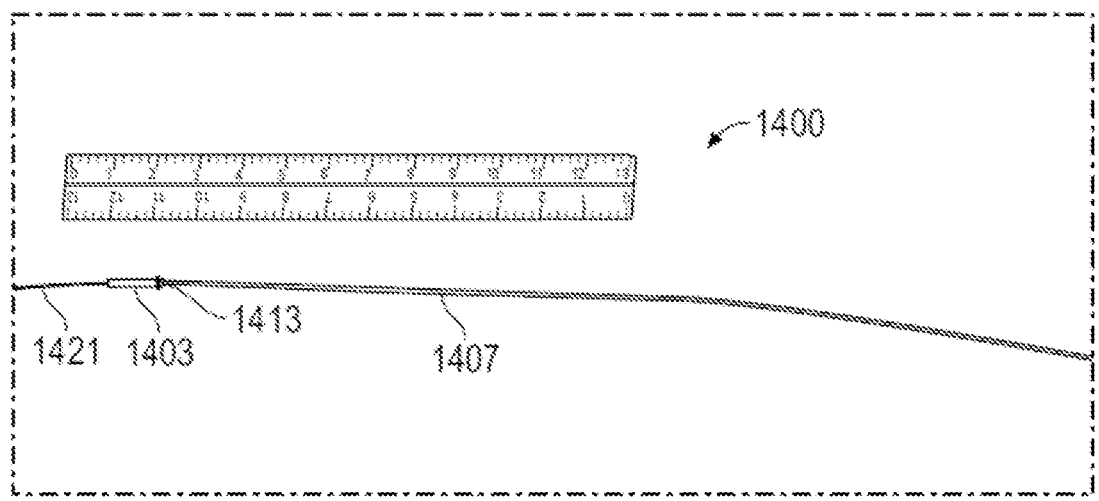

FIGS. 14A-14E illustrate one example of this method. FIG. 14A shows an example of an assembled apparatus 1400 that has been used to remove a clot, including the inversion support catheter 1407 and the knitted, flexible tube 1403. An internal support (e.g., wire or stylet 1421) is present in the inner lumen of the flexible tube, which is inverted into the lumen of the inversion support catheter. In FIG. 14A, the device may have been used to grab and secure a clot, which would be held within the inverted flexible tube. The free end 1413 of the flexible tube includes a collar that is configured (e.g., by being stiffer than the flexile tube and/or by including protrusions, shapes, etc.) to prevent it from inverting into the inversion support catheter.

Figure 14B:
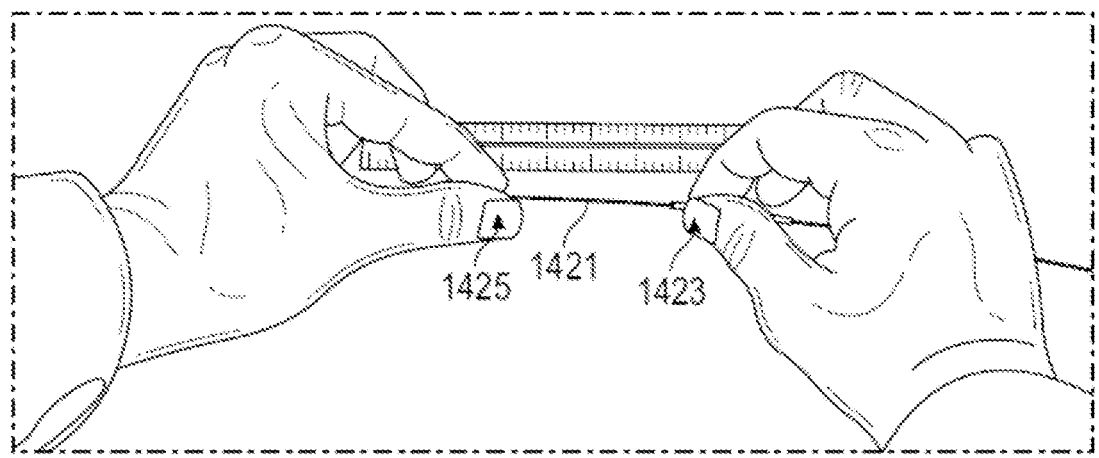
Figure 14C:
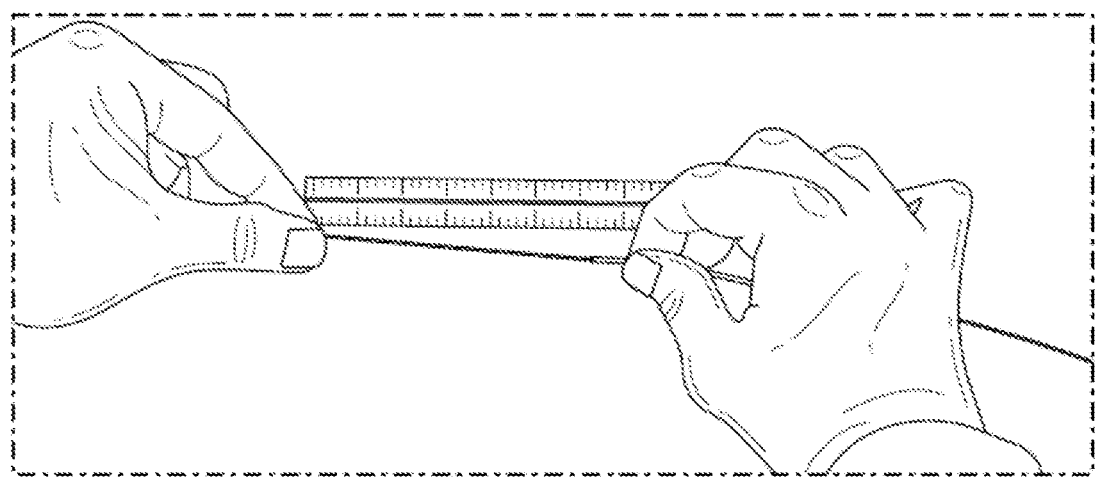

In order to reset the flexible tube so that the assembly of flexible tube, puller (not shown) and inversion support catheter may be re-inserted into the patient and used to remove additional material, the flexible tube may be compressed (e.g., loops or rungs of the woven or knitted flexible tube may be stacked against each other) within the inversion support tube. This may be achieved as shown in FIGS. 14B-14C by pulling the collar portion 1413 of the flexible tube proximally while holding, pinning or otherwise immobilizing the distal end of the internal support (e.g., wire 1421). In FIGS. 14B-14C the distal end of the internal support is pinned by the fingers of the user's hands 1423, 1425. The inversion support catheter is free to slide over the internal support proximally as the collar portion of the flexible tube is pulled proximally (e.g. to the right in FIG. 14C). Alternatively or additionally the distal portion of the inversion support may be driven proximally while pinning the flexible tube to the outer surface of the inversion support catheter and/or fixing the position of the pusher. The inversion support catheter may be slid over the internal support for a short distance (e.g., between about 5% and about 25% of the length of the flexible tube when stretched, such as 1-10 inches, etc.). In some examples a stop may be coupled to the proximal end of the internal support to prevent the catheter from sliding proximally further than this short distance.

In some examples, the portion of the flexible tube within the inversion support catheter may be compressed (e.g., stacked) by pinning the portion of the flexible tube at the distal end of the inversion support catheter and pushing the puller (not shown in FIGS. 14A-14E), distally.

Figure 14D:
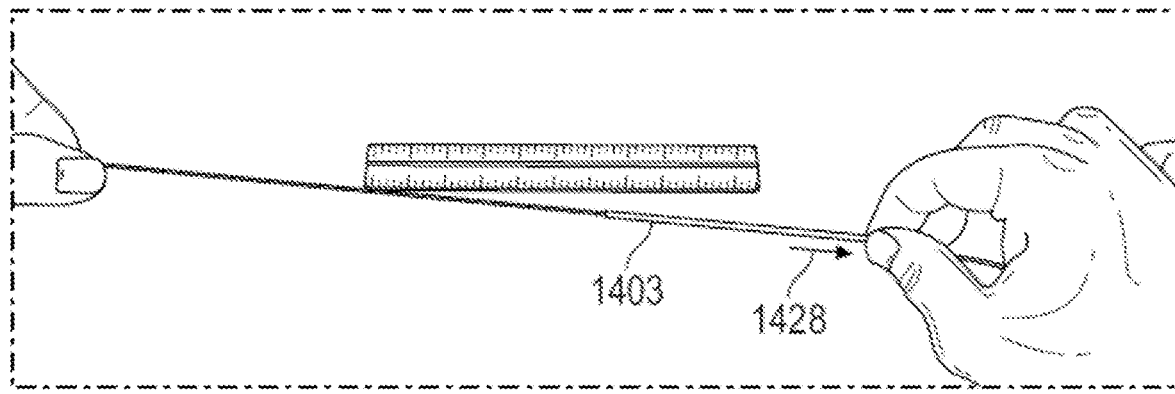
Figure 14E:
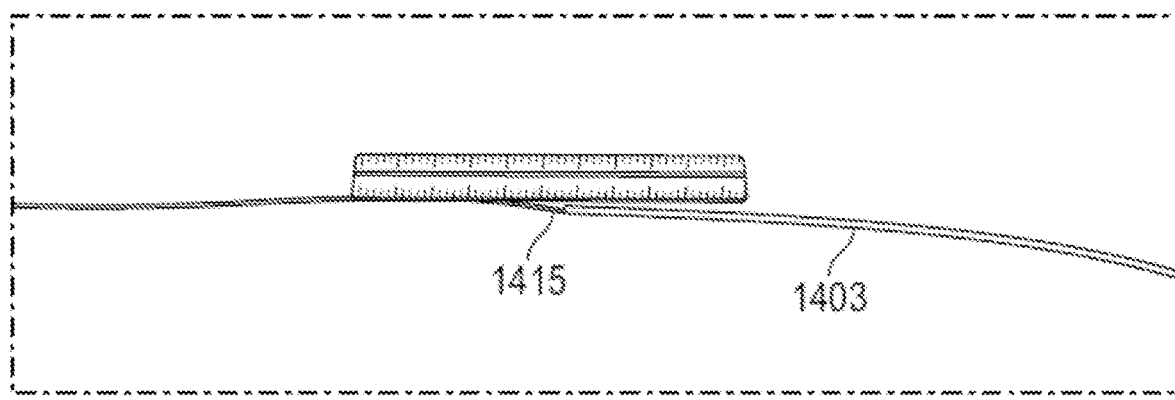

Once the flexible tube has been compressed within the inversion support catheter, the proximal end of the inversion support catheter may be secured relative to the flexible tube (e.g., pinned, held, etc.) and the free end of the flexible tube may be pulled 1428 proximally along the outside of the inversion support tube, as shown in FIG. 14D, causing the flexible tube to invert back over the distal opening of the inversion support tube. The puller (not shown) is not secured or held and is free to advance as the flexible tube is pulled over the distal end of the inversion support catheter. The entire flexible tube may be inverted back over the inversion support catheter in this manner, as shown in FIG. 14E. In FIG. 14E the flexible tube 1403 is shown fully removed and inverted back onto the outside of the inversion support catheter, the distal end of the puller 1415 is extending out of the inversion support catheter. The apparatus (the assembled inversion support catheter, puller and flexible tube) may then be inserted (e.g., after washing or removing clot material released by resetting the flexible tube) back into the body.

Figure 15A:
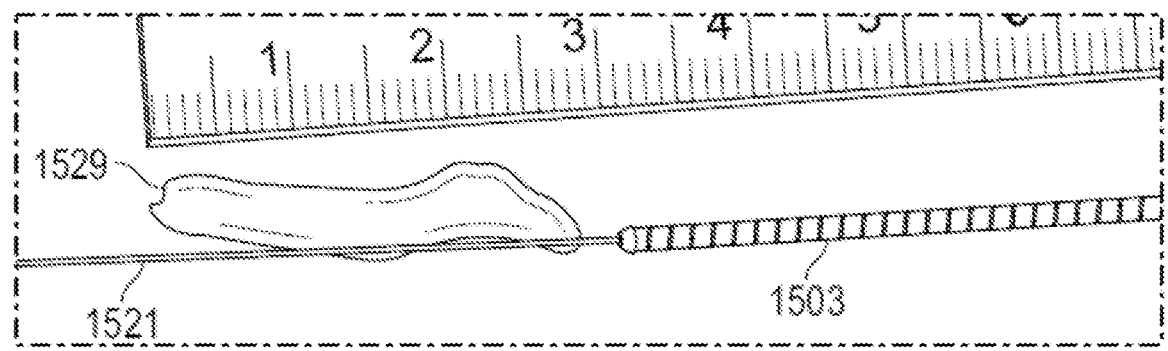
Figure 15B:
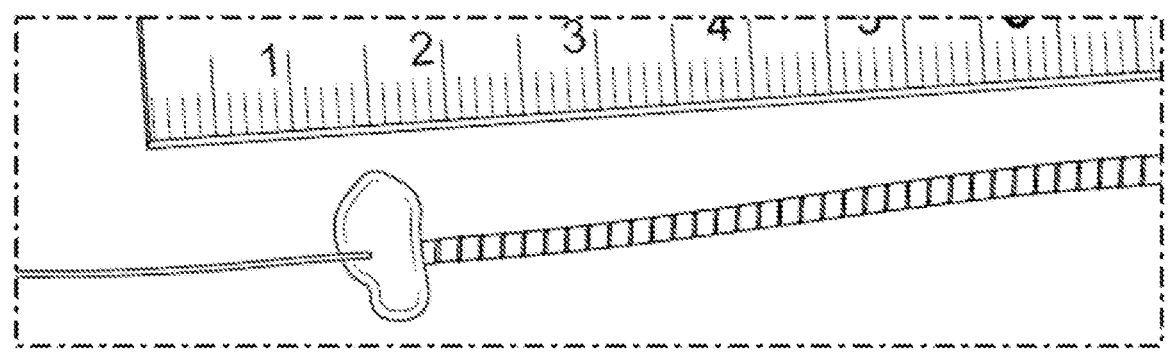
Figure 15C:
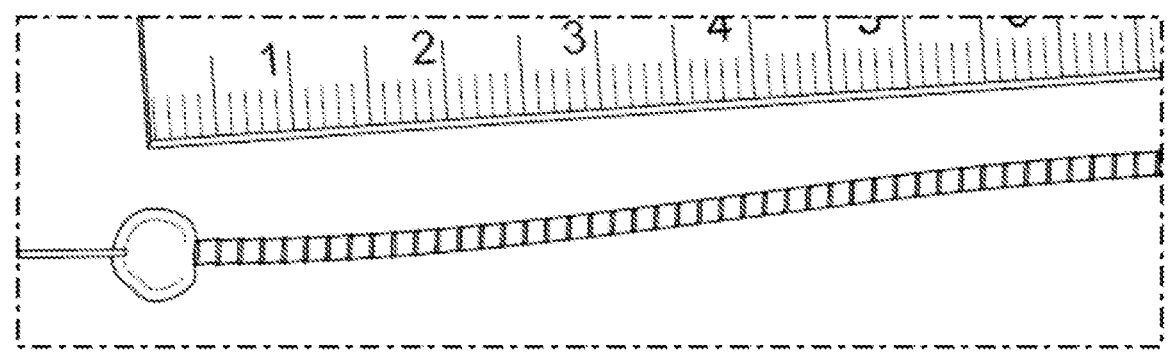
Figure 15D:
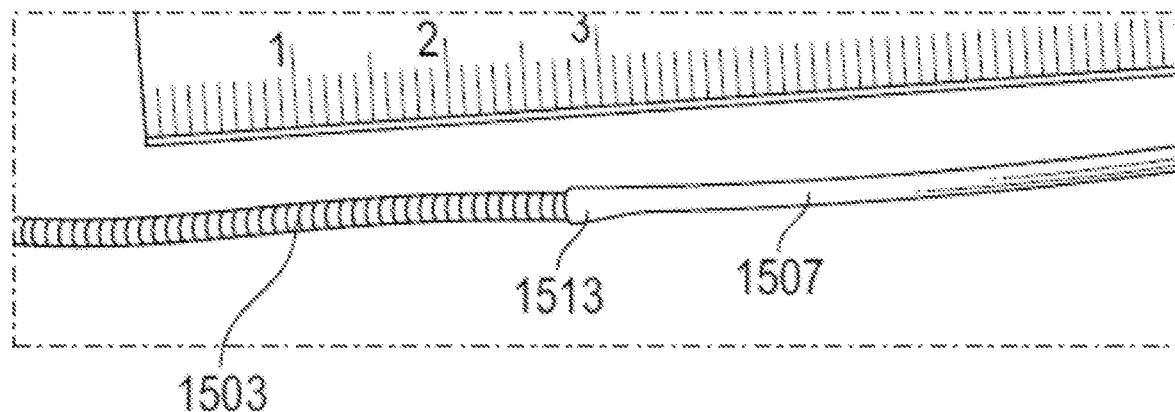

FIGS. 15A-15F illustrates another example of a method of removing clot using an inverting thrombectomy apparatus and/or resetting the apparatus for re-use. For example, FIGS. 15A-15C illustrate capturing a clot material using the inverting thrombectomy apparatus; although this example shows the apparatus grabbing clot outside of a body, the same method may be applied within a body lumen. In FIG. 15A, the apparatus is applied over a guidewire 1521 and navigated to the clot 1529 material. Once in proximity to the clot the apparatus may be actuated by pulling proximally on a puller (not shown) to pull the flexible tube 1504 from off of the outer surface of the inversion support catheter so that it inverts and rolls into the inversion support catheter, grabbing clot and carrying clot with the flexible tube as it inverts into the inversion support catheter. This is shown in FIGS. 15B-15D. In some examples the inversion support catheter may include an expandable funnel at its distal end (not shown). Once the majority of the flexible tube is inverted (and/or once the clot material is completely removed, when in a vessel), the apparatus may be removed from the body lumen (in examples where this is performed in a body lumen) and the device may be reset as described above, and as shown in FIGS. 15E-15F. FIG. 15D shows the inverting atherectomy apparatus after it has completely engulfed a clot material. The clot is compressed within the lumen of the flexible tube that is also within the inversion support catheter 1507.

Figure 15E:
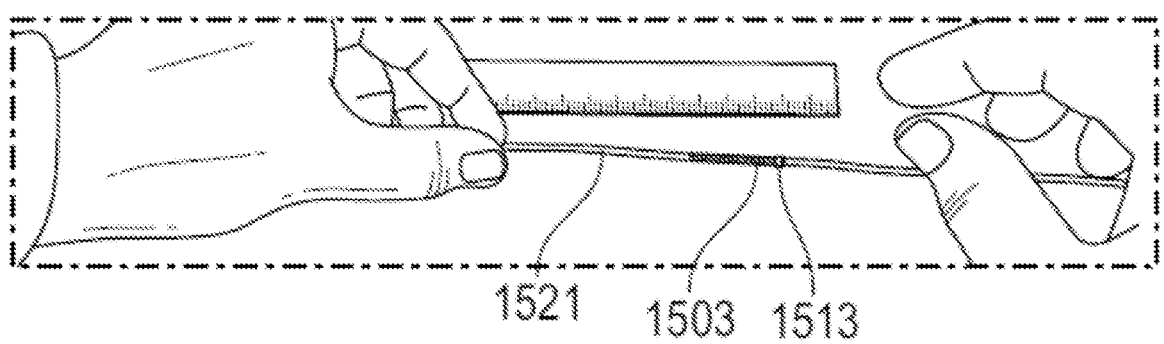
Figure 15F:
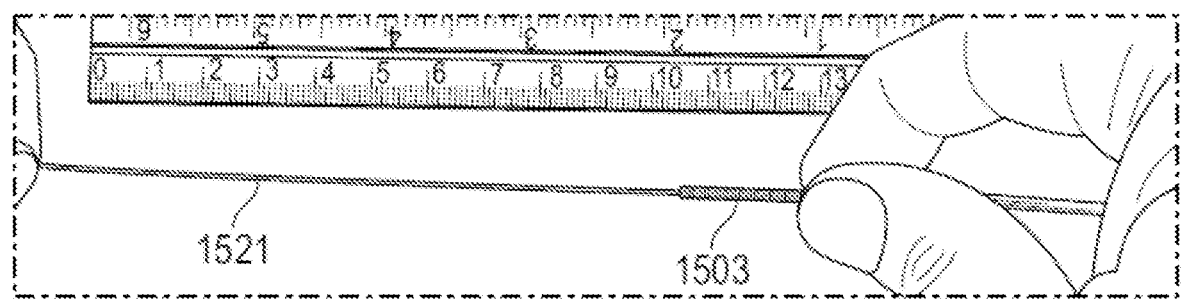
Figure 15G:
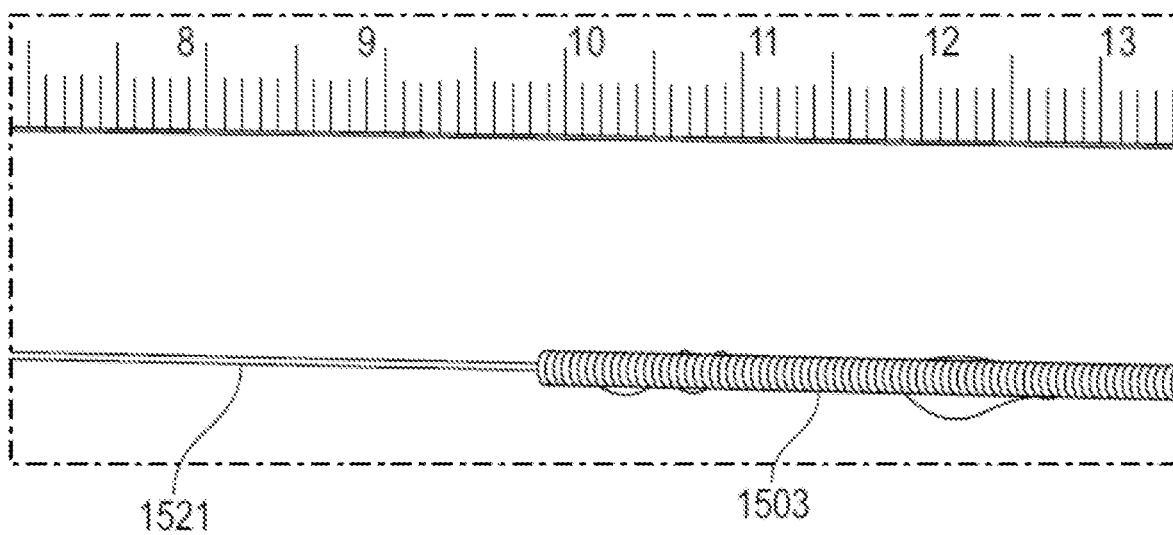
Figure 15H:
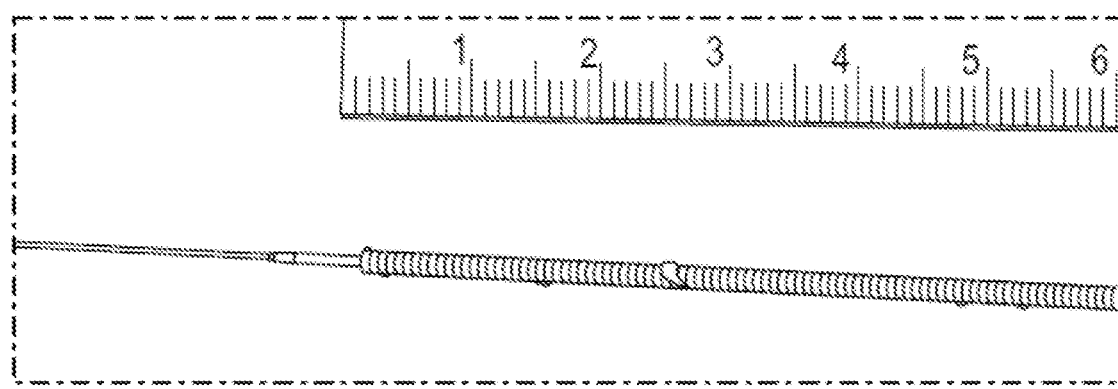

FIGS. 15E-15H illustrate resetting of the flexible tube of the inverting atherectomy apparatus as described in FIGS. 14A-14E. For example, in FIGS. 15A-15F the portion of the flexible tube within the lumen of the inversion support catheter is compressed, in this example by pinning the internal support (wire 1521) with one hand, and gasping the flexible tube 1503, e.g., by a cuff region 1513, as shown in FIGS. 15E and 15F. The inversion support catheter is not pinned but is initially free to slide over the internal support, while pulling the cuff region of the flexible tube proximally, as shown in FIG. 15F. Once the flexible tube has been compressed within the lumen of the inversion support catheter, the inversion support catheter may be pinned or held relative to the flexible tube, and the cuff region may be again (or continued to be) pulled proximally, so that it is pulled out of the distal end opening of the inversion support catheter and rolls and inverts over the inversion support catheter, as shown in FIG. 15G, until the entire flexible tube has been inverted back over the inversion support catheter, as shown in FIG. 15H. FIG. 15H also shows the clot material on the (now external) flexible tube. This material may be sampled and/or washed off as described below in relation to FIGS. 17A-17B.

Figure 16A:
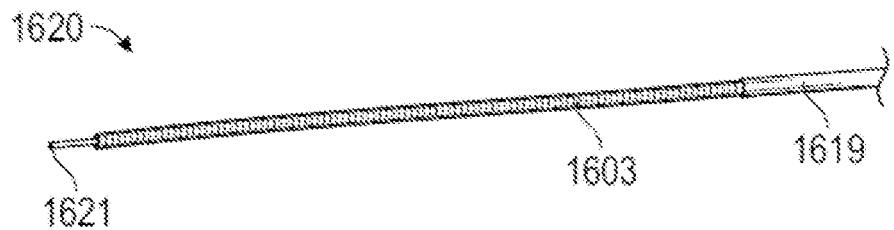
Figure 16B:
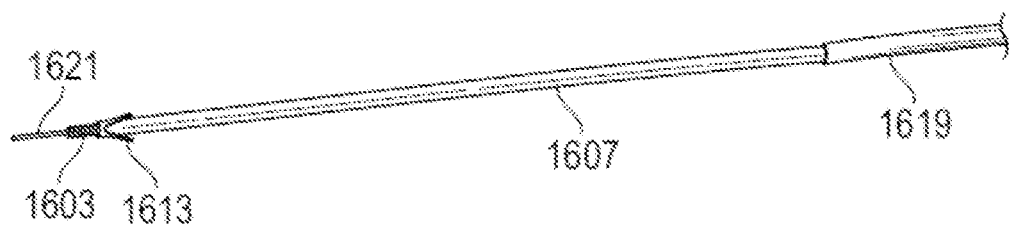
Figure 16C:
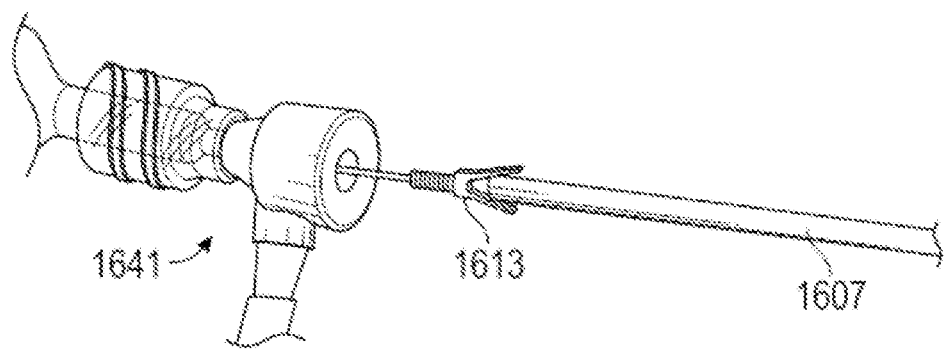
Figure 16D:
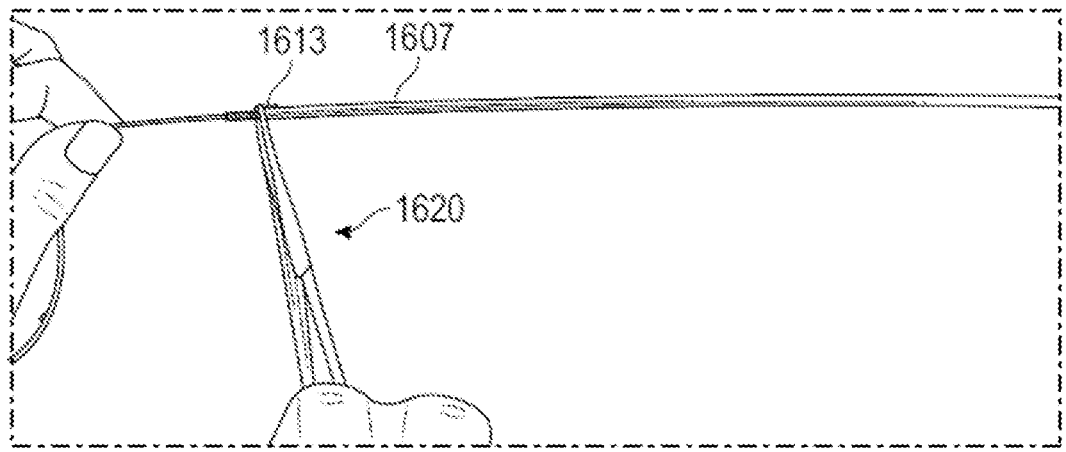
Figure 16E:
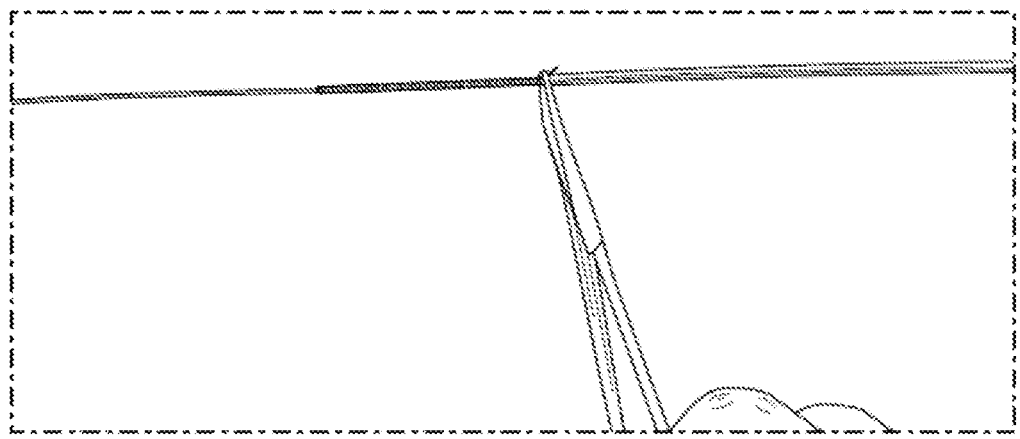
Figure 16F:
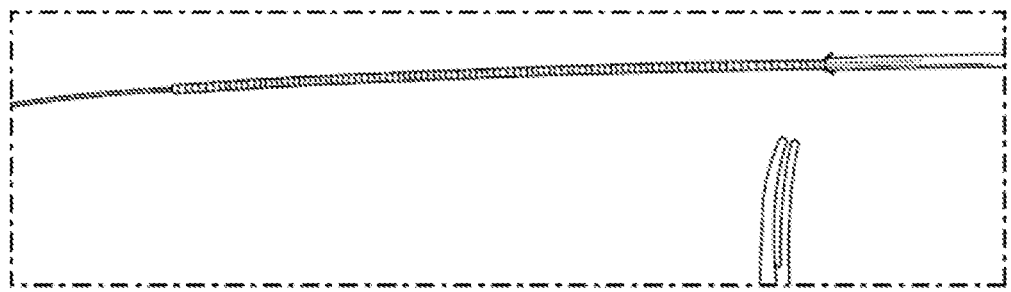

Although the method illustrated in FIGS. 14A-14E and 15A-15H show the user manually holding and pulling the free end of the flexible tube (e.g., a cuff region), in some examples it may be easier or preferred to use a manipulating member or tool to grasp and pull the free end. Any appropriate manipulating member may be used, for example a forceps or grasper. FIGS. 16A-16F illustrate this example. FIG. 16A show an inverting thrombectomy apparatus including a knitted flexible tube inverted over an inversion support catheter in the initial, loaded, configuration. The apparatus also includes an outer (e.g., delivery) catheter 1619 from which the inversion support catheter 1607 and flexible tube 1603 are extended, as shown. In FIG. 16A the device is shown positioned over a guidewire 1621. Once the device has been used to remove material, the flexible tube 1603 is shown mostly inverted into the inversion support catheter 1607 as shown in FIG. 16B. The device may then be removed from the body (e.g., out of a sheath hub 1641) as shown in FIG. 16C. FIGS. 16D-16F illustrate resetting of the flexible tube outside of the inversion support catheter by using a forceps 1620 to pull the cuff 1613 of the flexible tube, first to compress the flexible tube within the inversion support catheter (as shown in FIG. 16D), then to pin the end of the inversion support catheter and pull and invert the flexible tube over the outside of the inversion support catheter, as shown in FIGS. 16E-16F until it is fully inverted, reset and ready to be used again.

After use the flexible tube may be washed, as illustrated in FIGS. 17A-17B, e.g. be submersion into a sterile solution (e.g., water). In some examples, the apparatus may be sprayed. In any of these examples, the apparatus may be sterilized before re-using, but when reusing on the same patient immediately, within the same sterile field, additional sterilization may not be necessary. For example, the reset device may be washed with alcohol. The apparatus may be re-loaded into the body, e.g., through the sheath hub, to remove additional material.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

It should be appreciated that all combinations of the foregoing concepts and additional concepts discussed in greater detail below (provided such concepts are not mutually inconsistent) are contemplated as being part of the inventive subject matter disclosed herein and may be used to achieve the benefits described herein.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one example, the features and elements so described or shown can apply to other examples. It will also be appreciated by those of skill in the art that references to a structure or feature that is disposed "adjacent" another feature may have portions that overlap or underlie the adjacent feature.

Terminology used herein is for the purpose of describing particular examples only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative examples are described above, any of a number of changes may be made to various examples without departing from the scope of the invention as described by the claims. For example, the order in which various described method steps are performed may often be changed in alternative examples, and in other alternative examples one or more method steps may be skipped altogether. Optional features of various device and system examples may be included in some examples and not in others. Therefore, the foregoing description is provided primarily for exemplary purposes and should not be interpreted to limit the scope of the invention as it is set forth in the claims.

The examples and illustrations included herein show, by way of illustration and not of limitation, specific examples in which the subject matter may be practiced. As mentioned, other examples may be utilized and derived there from, such that structural and logical substitutions and changes may be made without departing from the scope of this disclosure. Such examples of the inventive subject matter may be referred to herein individually or collectively by the term "invention" merely for convenience and without intending to voluntarily limit the scope of this application to any single invention or inventive concept, if more than one is, in fact, disclosed. Thus, although specific examples have been illustrated and described herein, any arrangement calculated to achieve the same purpose may be substituted for the specific examples shown. This disclosure is intended to cover any and all adaptations or variations of various examples. Combinations of the above examples, and other examples not specifically described herein, will be apparent to those of skill in the art upon reviewing the above description.

What is claimed is:

1. An introducer apparatus, the apparatus comprising:
a flexible knitted or woven tube;
a puller coupled to one end of the knitted or woven tube;
an outer cover extending over the knitted or woven tube;
an inner cover extending at least partially within a lumen of the knitted or woven tube;
wherein the flexible knitted or woven tube is longitudinally movable relative to the outer cover and the inner cover; and
a handle portion continuous with the outer cover and the inner cover, wherein the handle portion comprise a frangible region that is configured to be broken along a predetermined tear line extending through the handle portion, the inner cover and the outer cover so that the handle portion, inner cover and outer cover are peeled away from the flexible knitted or woven tube after breaking the frangible region.

2. The apparatus of claim 1, wherein the outer cover comprises a distal end configured to mate with a sheath hub so that the flexible knitted or woven tube is driven out of the introducer apparatus and into the sheath hub.

3. The apparatus of claim 2, wherein the distal end comprises a mating engagement configured to mate with the sheath hub.

4. The apparatus of claim 1, wherein the handle portion comprises an opening through the handle portion that is continuous with the lumen of the knitted or woven tube.

5. The apparatus of claim 1, further comprising a second tear line extending from the frangible region through both the outer cover and the inner cover.

6. The apparatus of claim 1, wherein the predetermined tear line extends from a proximal end to a distal end of the introducer apparatus, wherein the handle portion is on the proximal end of the introducer apparatus.

7. The apparatus of claim 1, wherein the handle portion is configured to be grasped by one hand.

8. The apparatus of claim 1, wherein the handle portion is T-shaped.

9. The apparatus of claim 1, wherein a distal end of the outer cover is tapered.

10. The apparatus of claim 1, wherein the predetermined tear line is perforated.

11. An introducer apparatus, the apparatus comprising:
a flexible knitted or woven tube;
a puller coupled to one end of the knitted or woven tube, the woven tube including a portion inverted over an end of the puller;
an outer cover extending over the knitted or woven tube;
an inner cover extending at least partially between at least a portion of the inverted portion of the knitted or woven tube and the puller;
wherein the flexible knitted or woven tube is longitudinally movable relative to the outer cover and the inner cover; and
a handle portion connected to the outer cover and the inner cover, wherein the handle portion comprise a predetermined tear line extending through the handle portion, the inner cover and the outer cover so that the handle portion, inner cover and outer cover are peeled away from the flexible knitted or woven tube after breaking the frangible region.

12. The apparatus of claim 11, wherein the outer cover comprises a distal end configured to mate with a sheath hub so that the flexible knitted or woven tube is driven out of the introducer apparatus and into the sheath hub.

13. The apparatus of claim 12, wherein the distal end comprises a mating engagement configured to mate with the sheath hub.

14. The apparatus of claim 11, wherein the handle portion comprises an opening though the handle portion that is continuous with the lumen of the knitted or woven tube.

15. The apparatus of claim 11, further comprising a second tear line extending from the frangible region through both the outer cover and the inner cover.

16. The apparatus of claim 11, wherein the predetermined tear line extends from a proximal end to a distal end of the introducer apparatus, wherein the handle portion is on the proximal end of the introducer apparatus.

17. The apparatus of claim 11, wherein the handle portion is configured to be grasped by one hand.

18. The apparatus of claim 11, wherein a distal end of the outer cover is tapered.

19. The apparatus of claim 11, wherein the predetermined tear line is perforated.

20. An introducer apparatus, the apparatus comprising:
a flexible knitted or woven tube;
a puller coupled to one end of the knitted or woven tube, the woven tube including a portion inverted over an end of the puller;
an outer cover extending over the knitted or woven tube;
an inner cover extending at least partially between at least a portion of the inverted portion of the knitted or woven tube and the puller;
wherein the flexible knitted or woven tube is longitudinally movable relative to the outer cover and the inner cover; and
a handle portion connected to the outer cover and the inner cover, wherein the handle portion comprises a first predetermined tear line and a second predetermined tear line, the first and the second predetermined tear lines extending through the handle portion, the inner cover and the outer cover.

* * * * *